United States Patent [19]
Mottola et al.

[11] Patent Number: 5,533,986
[45] Date of Patent: *Jul. 9, 1996

[54] CATHETER APPARATUS WITH MEANS FOR SUBCUTANEOUS DELIVERY OF ANESTHETIC AGENT OR OTHER FLUID MEDICAMENT

[75] Inventors: Jim Mottola; Arlin D. Nelson, both of South Jordan; Chris Durham, Salt Lake City, all of Utah

[73] Assignee: Merit Medical Systems, Inc., South Jordan, Utah

[ * ] Notice: The term of this patent shall not extend beyond the expiration date of pat. No. 5,405,334.

[21] Appl. No.: 417,824

[22] Filed: Apr. 6, 1995

Related U.S. Application Data

[63] Continuation-in-part of Ser. No. 198,625, Feb. 18, 1994, Pat. No. 5,405,334.

[51] Int. Cl.$^6$ .................................................. A61M 25/00
[52] U.S. Cl. ............................................................ 604/264
[58] Field of Search ........................... 604/53, 164, 264, 604/280, 281, 282, 283, 284

[56] References Cited

U.S. PATENT DOCUMENTS

| | | | |
|---|---|---|---|
| 1,968,997 | 8/1934 | Drucker | 604/164 |
| 3,670,729 | 6/1972 | Bennett et al. | 604/164 |
| 4,149,535 | 4/1979 | Volder | 604/164 |
| 4,581,019 | 4/1986 | Curelaru et al. | 604/164 |
| 4,865,593 | 9/1989 | Ogawa et al. | 604/264 |
| 5,125,904 | 6/1992 | Lee | 604/164 |
| 5,147,334 | 9/1992 | Moss | 604/264 |
| 5,250,038 | 10/1993 | Melker et al. | 604/264 |
| 5,254,104 | 10/1993 | Furlow et al. | 604/264 |
| 5,269,755 | 12/1993 | Bodicky | 604/53 |
| 5,282,785 | 2/1994 | Shapland et al. | 604/21 |
| 5,300,032 | 4/1994 | Hibbs et al. | 604/164 |

*Primary Examiner*—Manuel Mendez
*Attorney, Agent, or Firm*—Workman Nydegger Seeley

[57] ABSTRACT

A novel catheter apparatus for use in delivering an anesthetic agent or other fluid medicament to the portion of subcutaneous tissue through which a catheter device has been inserted into a patient, thereby allowing the catheter device to be retracted without causing pain or discomfort to the patient. The catheter device has an indwelling cannula adapted for insertion through subcutaneous tissue into a patient's body. A helical sheath is formed from an elongate band that is wrapped around the cannula in a helical fashion so as to be capable of being positioned within the subcutaneous tissue once the cannula has been inserted into the body. The helical sheath has formed therein a lumen into which the anesthetic agent or other fluid medicament can be delivered via a hub that is connected to the proximal end of the helical sheath. The helical sheath has formed therein a plurality of delivery holes that form a fluid communication path with the lumen. The delivery holes permit the anesthetic agent or fluid medicament to be delivered to the surrounding subcutaneous tissue.

20 Claims, 15 Drawing Sheets

CATHETER APPARATUS WITH MEANS FOR SUBCUTANEOUS DELIVERY OF ANESTHETIC AGENT OR OTHER FLUID MEDICAMENT

RELATED APPLICATION INFORMATION

This application is a continuation-in-part of U.S. application Ser. No. 08/198,625, filed on Feb. 18, 1994 now U.S. Pat. No. 5,405,334, which is incorporated herein by reference.

BACKGROUND OF THE INVENTION

1. Field of the Invention

This invention relates to a catheter apparatus with a means for subcutaneous delivery of anesthetic agents or other fluid medicaments, and more particularly to catheter apparatus having subcutaneous infusion ports that provide for the administration of a local anesthesia or other medicaments to an area of subcutaneous tissue through which a cannula has been inserted.

2. The Present State of the Art

Catheter devices are widely used for a variety of medical applications. Generally, a catheter is a hollow, tubular cannula that is capable of being inserted into canals, vessels, passageways, or other body cavities so as to permit injection or withdrawal of fluids, or to keep a passage open. Other catheter devices are used for controlling, directing and placing medical devices, such as intubation tubes or dilation catheters, into a body cavity, such as the trachea, a blood vessel, or the heart. These types of insertion catheters are commonly referred to as intubators, insertion sheaths, and/or dilators. Given that catheters are used for such a wide variety of applications, catheters are implemented in a variety of designs, shapes and sizes. However, when used, almost all catheters share the universal characteristic of having to be passed through the skin and subcutaneous tissue of the patient so as to be inserted into the proper body cavity.

Depending on the medical procedure, the catheter is very often left in the body cavity over a relatively long period of time. As such, the skin and subcutaneous tissue through which the catheter device is inserted often becomes very swollen and tender, and thus extremely sensitive. Consequently, when the catheter is eventually retracted from the patient, the patient will often experience great discomfort. This discomfort may agitate the patient and thereby hinder the ability of medical personnel to effectively retract the catheter and/or treat the patient.

For example, in a percutaneous transluminal coronary angioplasty (PTCA) procedure, a patient is administered a local anesthesia and an intravascular sheath introducer (a type of catheter device) is inserted through the patient's skin in the groin area and into the femoral artery. In so doing, the sheath introducer necessarily passes through the area of subcutaneous tissue that lies between the skin and the femoral artery. Once inserted, the sheath introducer catheter provides a means for introducing the dilation catheter for performing the PTCA procedure.

Following the PTCA procedure, the sheath introducer is usually left within the femoral artery for a period ranging between four to twenty-four hours. Typically, the sheath is left in place because blood thinning drugs, such as Heparin, are administered to the patient. The effects of such drugs must wear off before the sheath can be removed in order to avoid hemorrhaging problems. Similarly, the device may be left in the patient as a precaution, in case quick access to the femoral artery is needed due to subsequent complications, such as an abrupt closure of the artery. In any event, by the time the sheath is retracted, the patient's skin and subcutaneous tissue through which the catheter is inserted is typically very swollen, bruised and tender. Also, by this time, the numbing effects of the earlier administered local anesthesia have completely worn off. Consequently, as the sheath is retracted from the femoral artery, the subcutaneous tissue and the overlying skin, the patient can experience considerable pain.

Pain experienced during sheath removal is known to occasionally cause vasovagal syncope type reactions, which can potentially result in a variety of undesirable patient responses—including a drop in blood pressure and heart rate. This can be hazardous when it occurs so soon after the PTCA procedure, and may thus require treatment with intravenous Atropine, or other drugs. Pain may also cause the patient to become agitated, which makes it difficult for medical personnel to properly administer arterial compression. This can lead to a hematoma formation within the subcutaneous tissue adjacent to the catheter.

Although medical personnel can administer a local anesthesia to the area, this must be done with a hypodermic needle, which usually causes as much discomfort or pain as the actual retraction of the catheter device. Thus, there is not a medical device available which adequately relieves a patient's discomfort during catheter retraction, and there is a need to be able to administer a local anesthesia to the subcutaneous tissue surrounding a catheter device prior to the retraction of the device, in a relatively painless and easy manner.

BRIEF SUMMARY AND OBJECTS OF THE INVENTION

The apparatus of the present invention has been developed in response to the present state of the art, and in particular, in response to the problems involved with the pain and discomfort that is experienced by a patient when a catheter device is removed. Thus, it is an overall object of the present invention to provide an apparatus which provides for the ability to painlessly administer local anesthesia or other medicaments to an area of subcutaneous tissue through which a catheter device has been inserted.

A further object of the present invention is to provide an apparatus that permits subcutaneous delivery of such medicaments but which also prevents bodily fluids from entering the apparatus while it is inserted and remains within the patient's body.

Yet another important object of the present invention is to provide an anesthetizing catheter sheath apparatus that can be manufactured either as an integral part of a catheter device, or as an apparatus that can be detachably mounted to a catheter device.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

Briefly summarized, the foregoing and other objects are achieved with a catheter apparatus that is inserted into a patient's body through subcutaneous tissue. In one presently preferred embodiment, a sheath fits over the catheter and is designed for insertion together with the catheter through the subcutaneous tissue. Once the catheter device is inserted into the patient's body, the outer surface of the catheter device necessarily passes through the patient's skin and a portion of underlying, subcutaneous tissue. The sheath which is disposed on the outer surface of the catheter device is also thus inserted through the subcutaneous tissue. Prior to retracting the catheter device, medical personnel can administer an anesthetic agent by infusing it into the surrounding subcutaneous tissue from the anesthetizing sheath. In this way, the subcutaneous tissue will be numbed, and the patient will experience no pain while the catheter device is retracted. In addition to anesthetic agents, the sheath can also be used to deliver a wide variety of other types of fluid medicaments to the subcutaneous tissue. For instance, the sheath may be used to deliver topical antibacterial agents to the tissue.

In one presently preferred embodiment of the present invention, the anesthetizing sheath apparatus can be permanently mounted to the catheter device, and is thus manufactured as an integral part of the catheter device.

In another presently preferred embodiment of the present invention, the anesthetizing sheath can be detachably mountable to the outer surface of the catheter device. In this manner, the anesthetizing sheath can be designed for use with any of a wide variety of existing catheter devices already on the market, thereby increasing its versatility.

In a still further embodiment of the invention, rather than using a sheath, the outer wall of the catheter device is provided with a secondary lumen, into which the anesthetic agent is injected and from which the anesthetic agent is infused into surrounding subcutaneous tissue.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PREFERRED EMBODIMENTS

Figure 1:
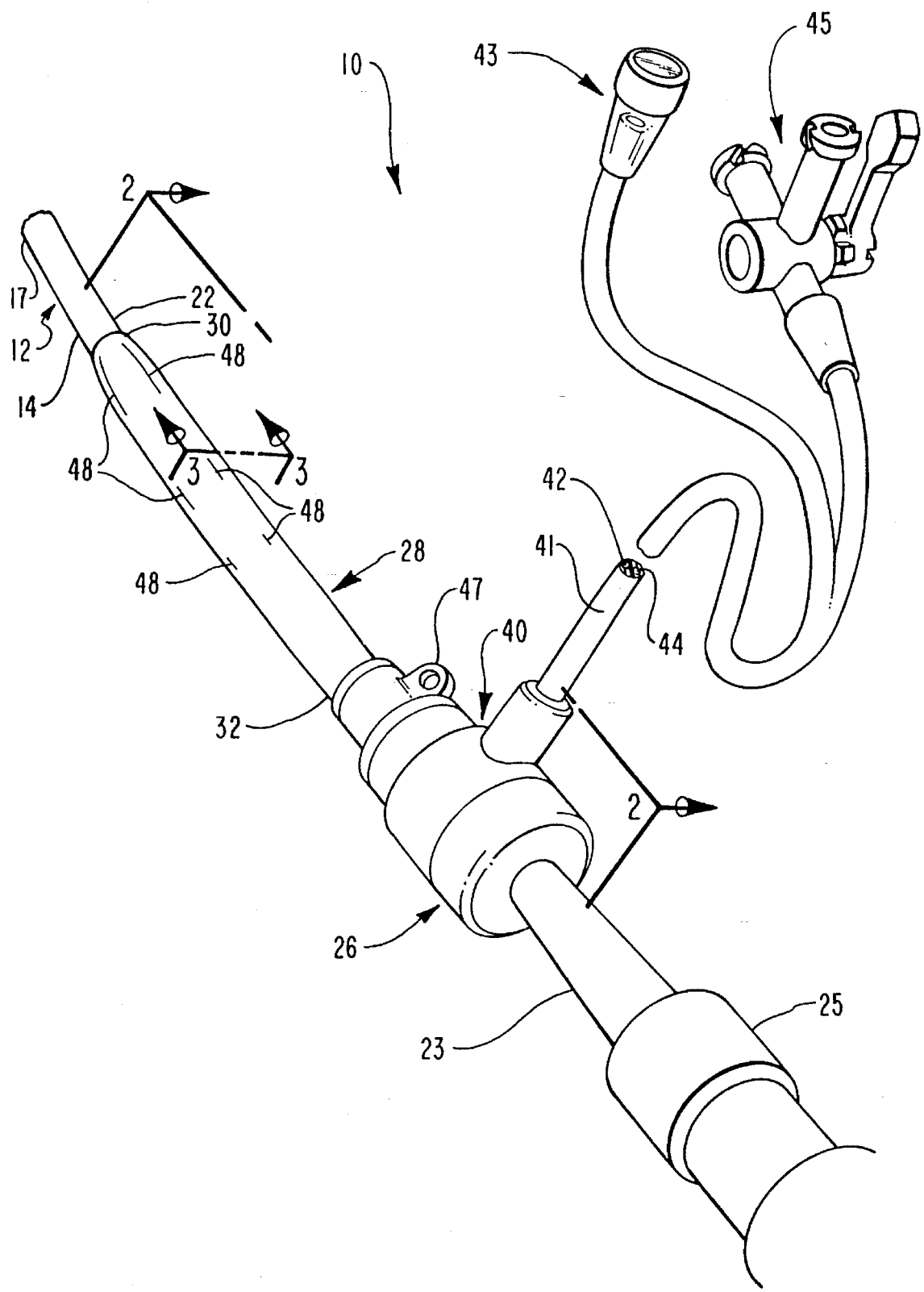
FIG. 1 is a perspective view illustrating one presently preferred embodiment of the catheter apparatus of the present invention.

Reference is next made to the drawings, wherein like parts are designated with like numerals throughout. Referring first to FIG. 1, one presently preferred embodiment of the invention is illustrated. FIG. 1 represents a perspective view of the catheter apparatus of the present invention, designated generally at 10. Catheter apparatus 10 includes a catheter means, as for example a catheter device designated generally at 12, for insertion through subcutaneous tissue. As used herein, the term catheter device is intended to broadly cover the general category of cannula-type devices referred to as catheters. Thus the term catheter device is intended to refer to any hollow, tubular cannula-type device that is capable of being inserted into canals, vessels, passageways, or other body cavities so as to permit injection or withdrawal of fluids, or to keep a passage open. Further, the term is intended to include insertion devices which are used for controlling, directing and placing medical devices, such as intubation tubes or dilation catheters, into a body cavity, such as the trachea, a blood vessel, or the heart, and which are commonly referred to as intubators, insertion sheaths, and/or dilators.

For purposes of example, the catheter device 12 illustrated in FIG. 1 is an insertion sheath comprised of an indwelling cannula 14 which is adapted for insertion through subcutaneous tissue and into a patient's body. As is better shown in FIG. 2, the cannula 14 is inserted into a patient's body (typically via a guide wire while the patient is numbed with a local anesthetic) so as to have a distal end 17 disposed within a body cavity, such as a blood vessel 16. As is shown, the cannula 14 necessarily passes through the patient's skin layer 18 and the area of subcutaneous tissue 20 that lies between the skin layer 18 and the body cavity, such as the blood vessel 16. Thus, once the cannula 14 is properly positioned, a portion 22 of the cannula 14 remains disposed within the area of subcutaneous tissue 20.

Once in place, the insertion sheath cannula 14 is used for controlling and directing the placement of another medical device, as for example a dilation catheter 24 for use in a PTCA procedure. The dilation catheter 24 is inserted into the hollow cannula 14 via the proximal hub end 26 of the catheter device 12, and the tubing 23 and connector 25 attached thereto. The proximal hub end 26 remains positioned outside of the body. Upon completion of the PTCA (or related) procedure, the dilation catheter 24 is removed from the cannula 14 through the proximal hub end 26. Typically, the distal end portion 17 of the cannula 14 then remains positioned within the patient, sometimes for as long as twenty-four hours. At the end of this time period (by which time all numbing effects of the local anesthesia have worn off) the patient's skin 18 and subcutaneous tissue 20 are swollen and very sensitive, and retraction of the cannula 14 can be extremely painful.

Referring again to FIG. 1, the catheter apparatus 10 of the present invention further comprises a sheath means, as for example a hollow cylindrical sleeve generally designated at 28, for placement onto at least a portion of the cannula 14 at a point intermediate of the distal end 17 and the proximal hub end 26. As is better shown in FIG. 2, the cylindrical sleeve 28 is positioned on the cannula 14 so as to be disposed on the portion 22 of cannula 14 that is surrounded by subcutaneous tissue 20 when the cannula 14 is indwelling within the patient's body.

Figure 2:
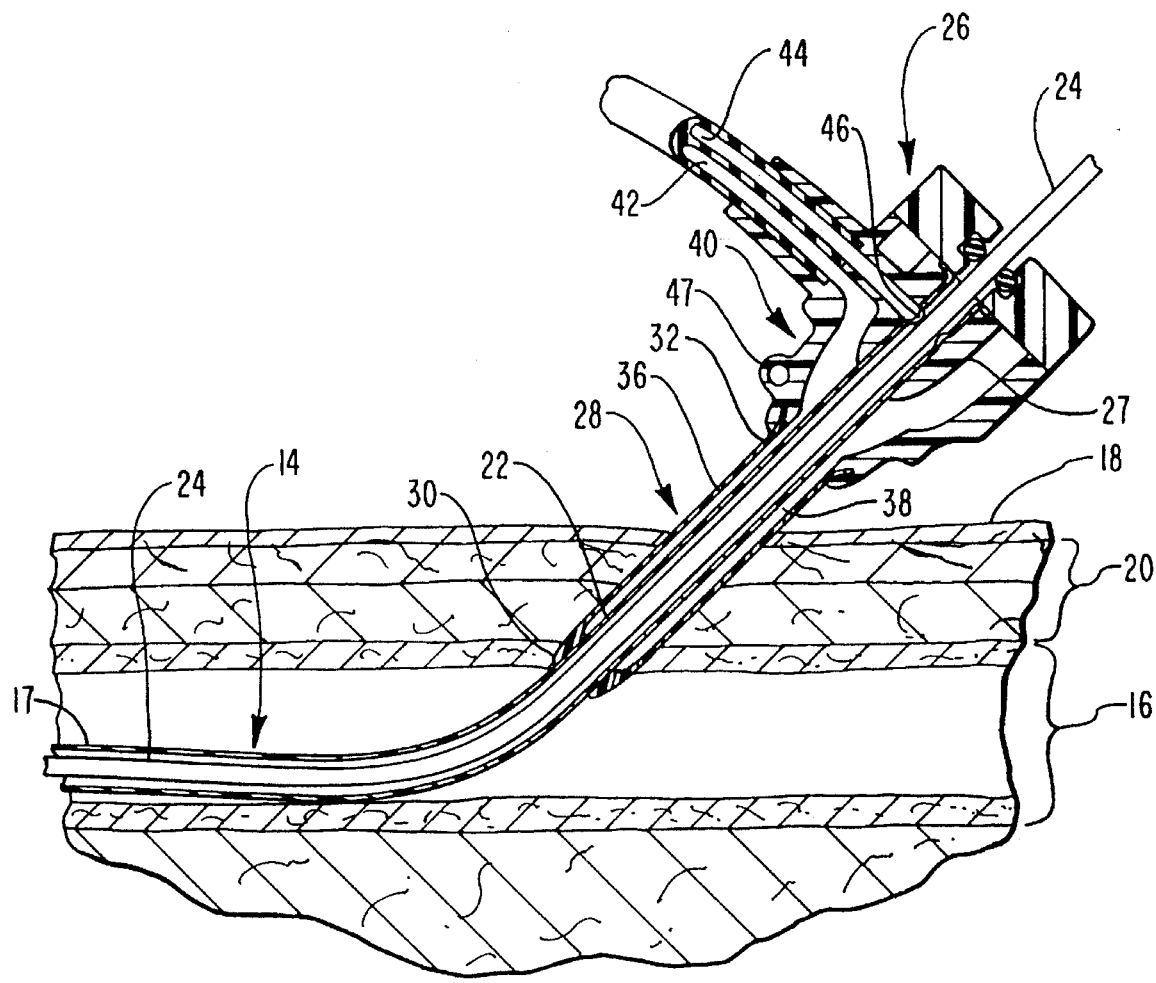
FIG. 2 is a cross-sectional view taken along line 2—2 in FIG. 1, and further illustrates the catheter apparatus of FIG. 1 disposed within a portion of a patient's body.
Figure 3:
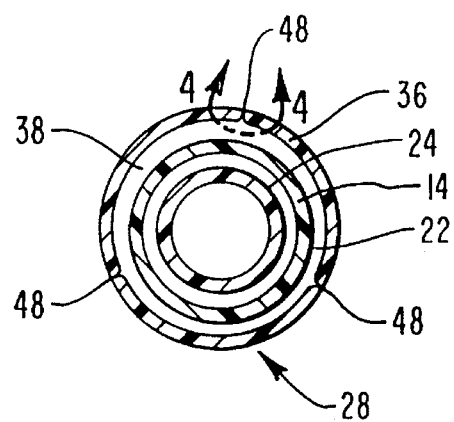
FIG. 3 is a cross-sectional view taken along line 3—3 in FIG. 1.

As is shown in the preferred embodiment of FIGS. 1 and 2, the cylindrical sleeve 28 has a distal end 30 and a proximal end 32. The cross-sectional view of FIG. 3 illustrates how hollow cylindrical sleeve 28 has an inner diameter which is greater than the outer diameter of cannula 14, and how cylindrical sleeve 28 is positioned on cannula 14 so as to be concentric with the cannula 14. Preferably, distal end 30 of cylindrical sleeve 28 is tapered where it terminates on the outer surface of cannula 14 so that the cylindrical sleeve 28 can be inserted with little or no trauma through the outer skin layer 18 and subcutaneous tissue 20. This tapered distal end 30 is best seen in FIG. 2.

The sheath means is further comprised of a means for sealing the sheath means in a fluid tight manner around the cannula 14 so as to prevent fluids, such as blood from the body, from escaping between the cannula 14 and the sheath means. In the embodiment of FIGS. 1 and 2, for example, this sealing function is accomplished by permanently affixing the cylindrical sleeve 28 over the outer surface 22 of the cannula 14. Thus, in this embodiment, the distal end 30 of the cylindrical sleeve 28 is fused, or otherwise suitably affixed, to the cannula 14. By so doing, fluids are prevented from entering the space or interior lumen 38 between the outer surface of the cannula 14 and the cylindrical sleeve 28.

The sheath means, as for example cylindrical sleeve 28, is further comprised of a means for delivering fluid medicament, such as an anesthetic agent (not shown), to essentially only that portion of subcutaneous tissue 20 that surrounds the sheath means. Delivery of fluid medicament is accomplished, for example, by way of the interior lumen 38 running from the distal end 30 to the proximal end 32 of the cylindrical sleeve 28. Delivery of fluid medicament is also aided by a hub means for delivering the fluid medicament to the interior lumen 38, and a plurality of valve means for communicating the fluid medicament from the interior lumen 38 to the subcutaneous tissue surrounding the sheath means.

By way of example, FIG. 2 illustrates cylindrical sleeve 28 as being comprised of a single cylindrical wall 36. In this particular embodiment, the interior lumen 38 is formed between the cylindrical wall 36 and the outer surface of the cannula 14. Interior lumen 38 is also shown in the cross-sectional view of FIG. 3.

By way of further example, FIGS. 1 and 2 illustrate how the hub means can be comprised of a hub 40 that is joined in a fluid tight manner to the proximal end 32 of the cylindrical sleeve 28, and to the proximal hub end 27 of the cannula 14. Hub 40 further comprises, for example, a first passageway means, such as a first hub lumen 42, for communicating the fluid medicament to the interior lumen 38. In addition, hub 40 comprises a second passageway means, such as second lumen 44, for providing fluid communication to the cannula 14 via a cannula access hole 46. FIG. 1 illustrates how the first and second hub lumens 42, 44 are preferably coupled to multi-lumen tube 41. Multi-lumen tube 41 is branched such that first hub lumen 42 is coupled to an infusion port 43, and second hub lumen is coupled to an I.V. valve assembly 45. In this way, a medical technician can administer fluid medicament with a syringe to the interior lumen 38 using infusion port 43.

By way of further example, FIG. 1 illustrates how the plurality of valve means are preferably comprised of a plurality of one way valve means spaced along the cylindrical sleeve 28. The one-way valve means not only allow the fluid medicament to be communicated from the interior lumen 38 to the subcutaneous tissue 20, but also act so as to prevent bodily fluids from entering the interior lumen 38. The one way valve function is provided by a plurality of one way slits 48 placed uniformly about the cylindrical sleeve 28. Because the width of the subcutaneous tissue 20 will vary from patient to patient, it is possible that the distal end 30 of the cylindrical sleeve 28, along with some of the slits 48, could be disposed within the blood vessel 16. In this situation, the one way slits 48 positioned within the portion of subcutaneous tissue 20 will properly communicate the anesthetic agent to the tissue 20, but any of the one way slits 48 that are located within the blood vessel 16 will prevent bodily fluids, such as blood, from entering the interior lumen 38.

As is further shown in FIG. 1, each slit 48 is preferably made longitudinally along the axis of the cylindrical sleeve 28. Slits 48 are uniformly located about the periphery of the cylindrical sleeve 28 so as to insure that the anesthetizing agent is evenly and uniformly delivered to the surrounding subcutaneous tissue 20. Further, the longitudinal length of each slit 48 changes depending on its location on the cylindrical sleeve 28. Preferably the slits 28 become progressively shorter as they near the proximal end 32 of the cylindrical sleeve 28. This variation in slit length is intended to help assure that fluid medicament is uniformly delivered from the proximal end 32 to the distal end 30 of sleeve 38. This may be especially important if one or more proximately located slits 48 are located outside of the patient's body during delivery of the fluid medicament.

Figure 4:
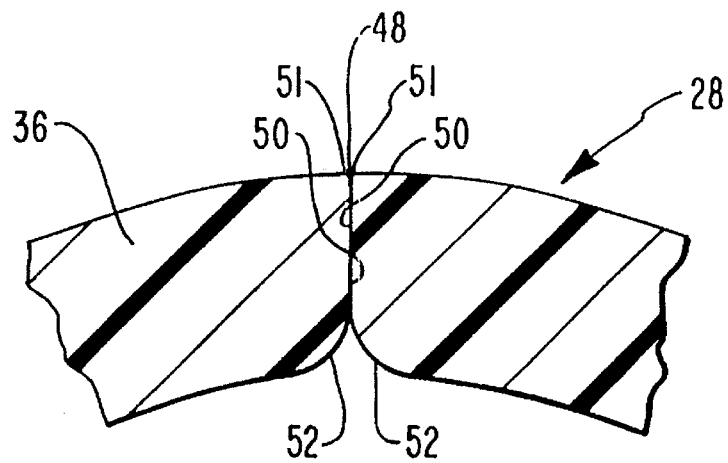
FIG. 4 is an enlarged cross-sectional view taken along line 4—4 of FIG. 3, showing a one way slit in a closed position.
Figure 5:
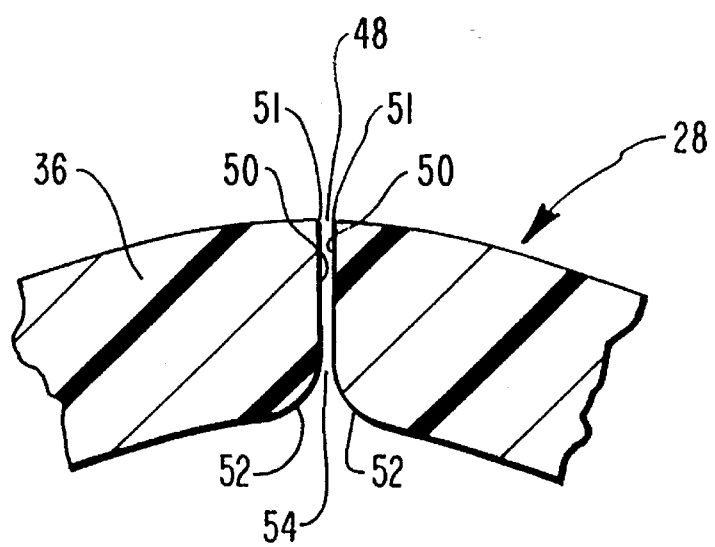
FIG. 5 is an enlarged cross-sectional view taken along line 4—4 of FIG. 3, showing a one way slit in an open position to permit infusion of anesthetic agent into surrounding subcutaneous tissue.

As is shown in FIGS. 3–5, each one way slit 48 extends completely through the cylindrical wall 36 of the cylindrical sleeve 28 so as to provide fluid communication with interior lumen 38. It is shown best in FIGS. 4 and 5 wherein each slit 48 is defined by opposed, aligned, normally abutting, parallel edges 50. FIG. 4 illustrates how a square portion 51 of the abutting edges 50 are normally engaged in a sealing relationship, and wherein the slit 48 is thereby in a closed position. The abutting edges 50 are further formed with rounded internal edge portions 52 that do not abut, but are spaced apart. In this closed position (shown in FIG. 4), the slit 48 will prevent any bodily fluids from entering the interior lumen 38.

Wall edges 50 are also capable of flexing outwardly from their closed position, responsive to a pressure generated within the interior lumen 38. In so doing, an orifice 54 is created, through which fluid such as the anesthetic agent, can flow. This open position is illustrated in FIG. 5. Thus, by applying a predetermined positive pressure to interior lumen 38, a fluid medicant such as an anesthetic agent is infused into the area of subcutaneous tissue 20 in which the cylindrical sleeve 28 is disposed, as shown in FIG. 2.

Slits 48 normally remain closed and wall edges 50 remain in an abutting position (FIG. 4). This requires that the cylindrical sleeve 28 have sufficient memory to return the slits 48 to the closed position after infusion of anesthetic agent is terminated. The cylindrical sleeve 28 may be constructed from a variety of materials with the required elasticity. Preferably, the cylindrical sleeve 28 is rigid enough to be easily inserted into the area of subcutaneous tissue 20 in conjunction with the cannula 14. At the same time, the cylindrical sleeve 28 should be flexible enough so as to conform to the movements of the patient, and such that the slits 48 exhibit the unidirectional fluid flow properties discussed above in connection with FIGS. 4 and 5.

In the preferred embodiment, cylindrical sleeve 28 is made from a polyurethane material. Also, Teflon, nylon or polyethylene materials may be suitable. The sleeve material can have a Shore A durometer in the range from about 80 to about 100 and Shore D durometer in the range of 40 to 70, and preferably will be in the range from about Shore D 40 to about 55.

It will be appreciated that the valve means may be comprised of a variety of equivalent structures. For instance, valve means could be comprised of a plurality of holes formed through the cylindrical wall 36 of the cylindrical sleeve 28. Further, this structure could provide a one way fluid flow function if the holes are made sufficiently large with respect to the width of interior lumen 38. In such an embodiment, the pressures exerted by bodily fluids, such as interstitial blood pressure, would compress the interior lumen 38 and thereby prevent back-flow of bodily fluids back into the interior lumen 38 through the holes. An illustrative example of such an embodiment is described in further detail below in connection with FIGS. 17A through 18B.

With continued reference to FIGS. 1 and 2, formed on the hub 40 near proximal end 32 of the cylindrical sleeve 28 is a suture attachment ring 47. Once the cylindrical sleeve 28, in conjunction with the insertion sheath cannula 14, has been positioned within the portion of subcutaneous tissue 20, the physician can suture, or otherwise attach, the cylindrical sleeve 28 to the patient via the suture attachment ring 47. In this manner, the cylindrical sleeve 28 will stay correctly positioned within the portion of subcutaneous tissue 20 during subsequent medical procedures, such as a PTCA. This insures that medical personnel can administer a fluid medicament, such as an anesthetic agent, to the subcutaneous tissue 20 without first having to reposition the cylindrical sleeve 28.

Figure 6:
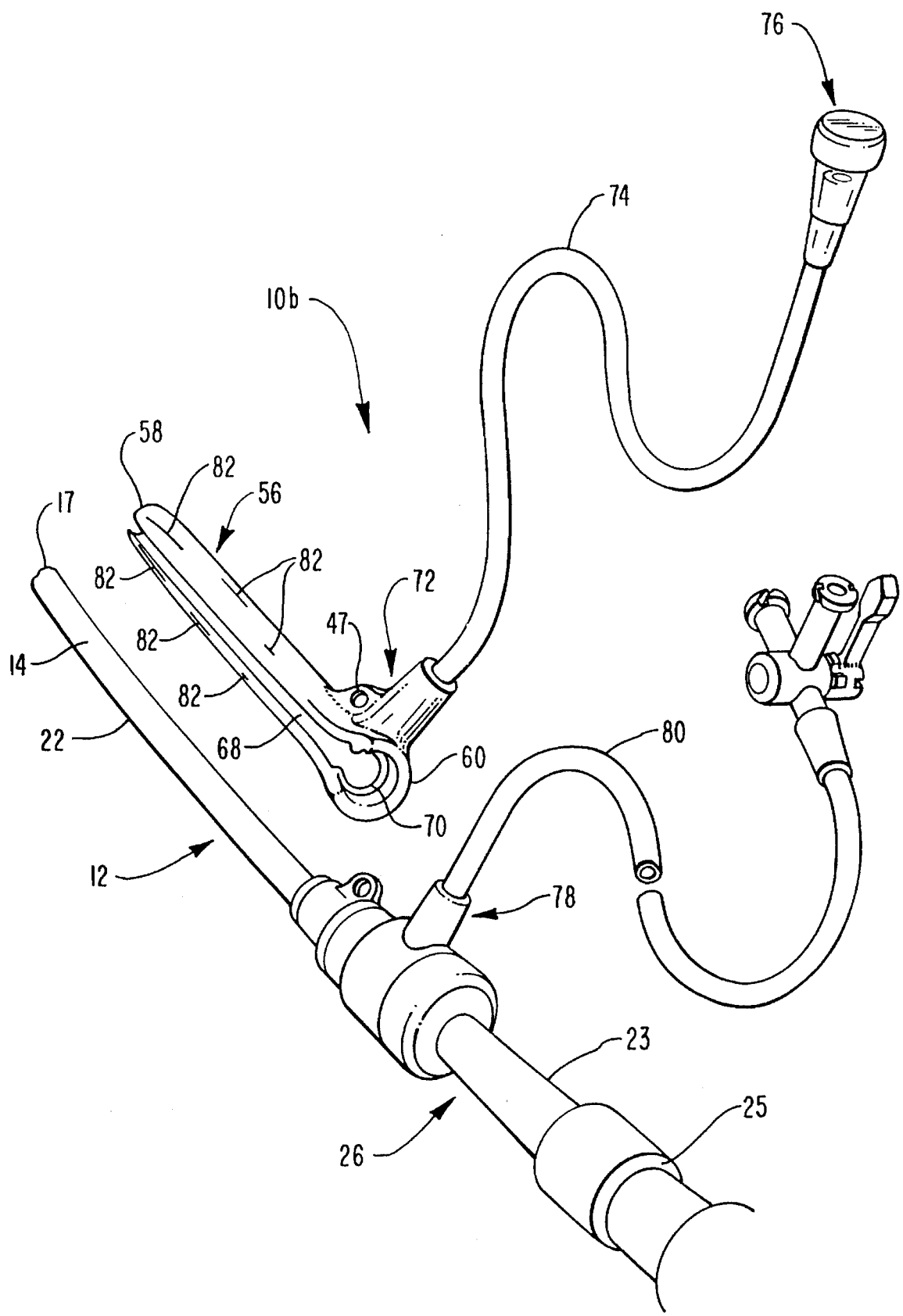
FIG. 6 is an exploded perspective view of another presently preferred embodiment of the catheter apparatus of the present invention.
Figure 7:
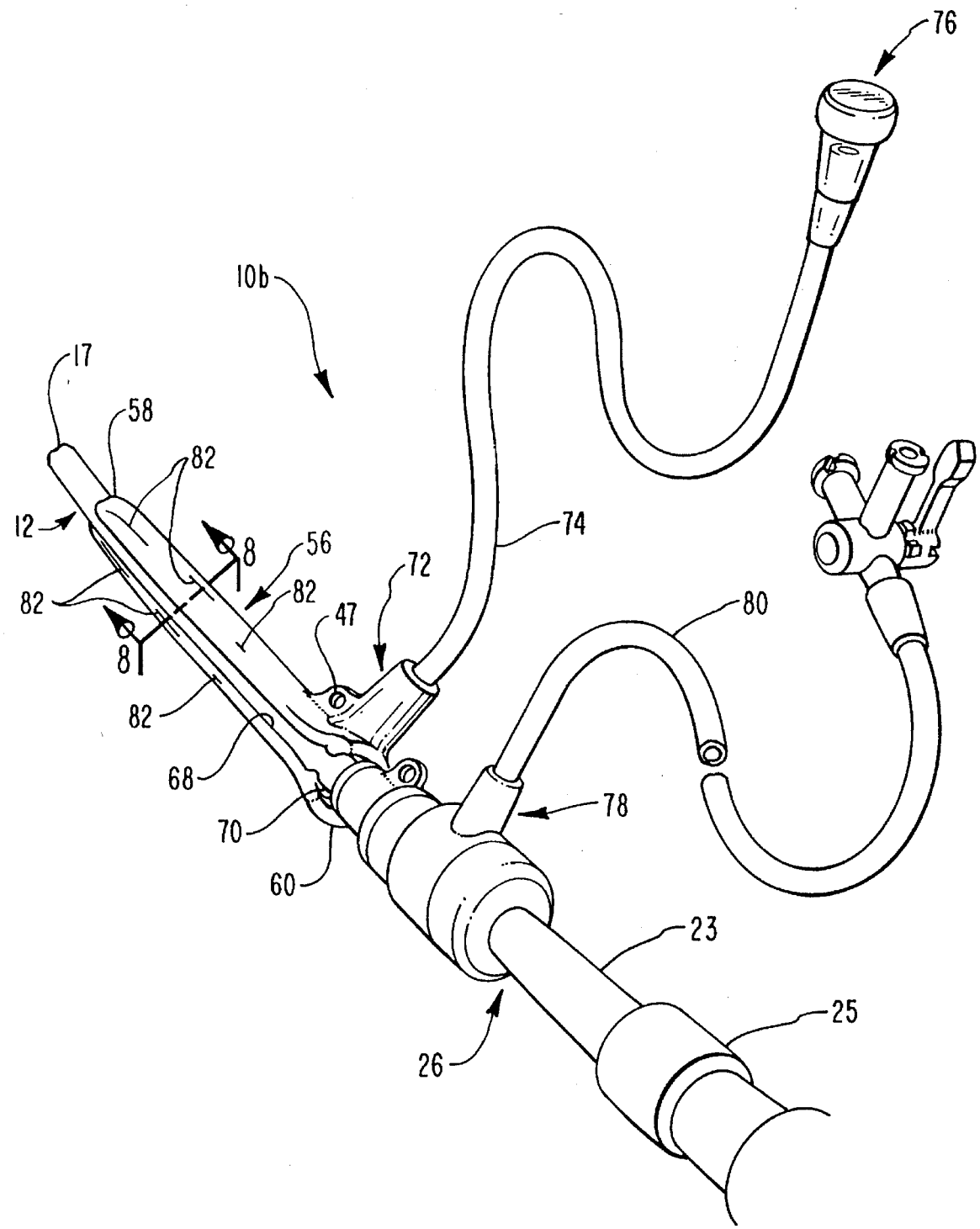
FIG. 7 is a perspective view of the anesthetizing sheath of FIG. 6 mounted to a catheter device.
Figure 8:
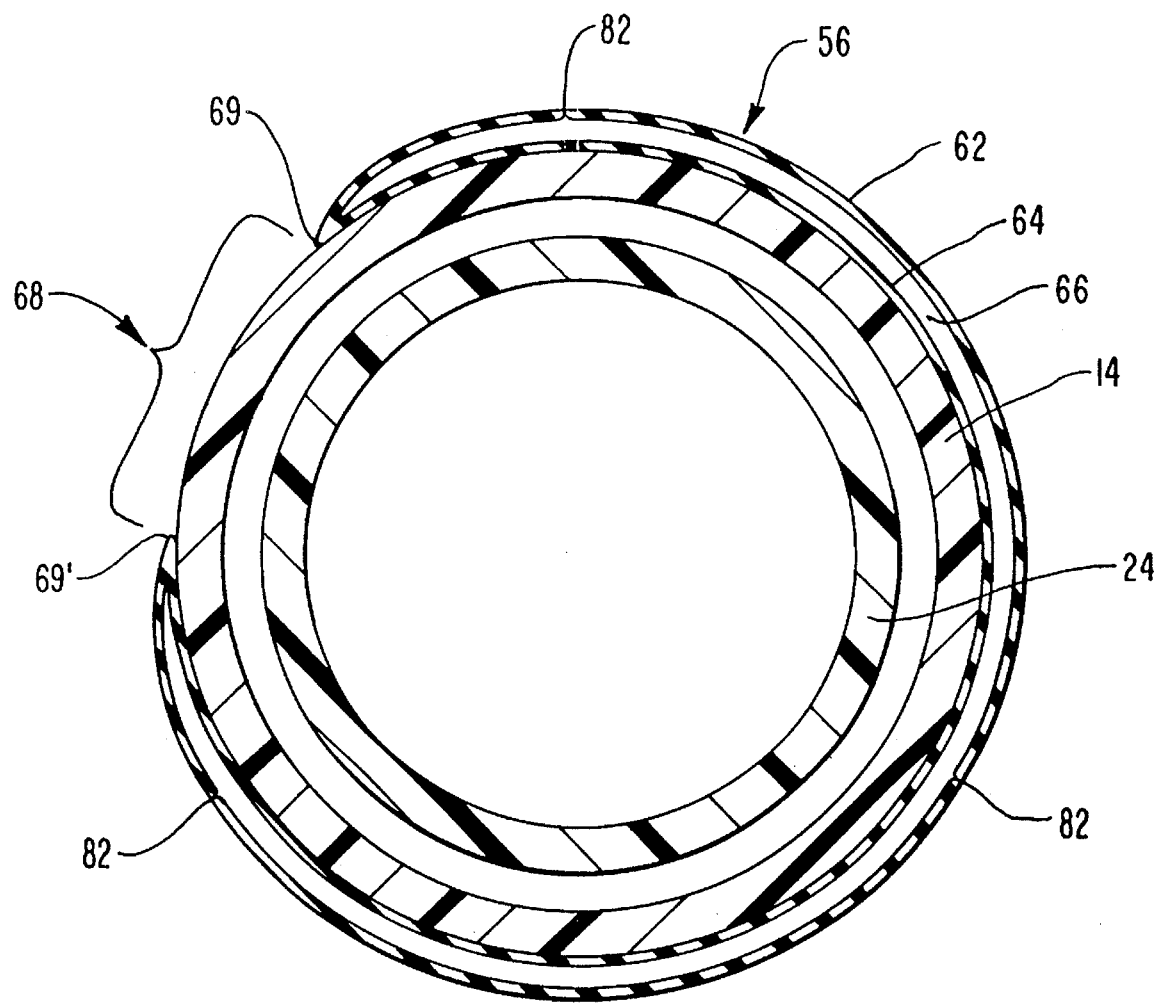
FIG. 8 is a cross-sectional view taken along line 8—8 in FIG. 7.

Another embodiment of the catheter apparatus of the present invention is illustrated in FIGS. 6 through 8, and is designated generally at 10b. Catheter apparatus 10b includes a catheter means, as for example a catheter device designated generally at 12 which is essentially the same as the catheter device discussed in conjunction with FIGS. 1 through 3. That discussion will not be repeated here.

The indwelling catheter apparatus 10b also comprises a a sheath means, as for example a hollow cylindrical sleeve 56, for placement onto at least a portion of the cannula 14 at a point intermediate of the distal end 17 and the proximal hub end 26 of the cannula 14. However, unlike the embodiment shown in FIGS. 1 through 3, the sheath means of FIGS. 6 through 8 can be selectively attached and detached to the cannula 22, as discussed in further detail below.

As is shown in FIGS. 6 and 7, cylindrical sleeve 56 has a distal end 58 and a proximal end 60. Hollow cylindrical sleeve 56 further has an inner diameter which is greater than the outer diameter of cannula 14. This relationship is also shown in the cross-sectional view of FIG. 8. Also shown in FIG. 8 is how cylindrical sleeve 56 is positioned, in a tight fitting manner, on cannula 14 so as to be concentric with the cannula 14. Preferably, distal end 58 of cylindrical sleeve 56 is tapered with respect to the outer surface 22 of cannula 14, so that the cylindrical sleeve 56 can be inserted with little or no trauma through the portion of subcutaneous tissue 20 when it is mounted to the cannula 14.

The cylindrical sleeve 56 further comprises a means for delivering fluid medicament, such as an anesthetic agent, to the subcutaneous tissue 20 surrounding the sleeve 56. The fluid medicament delivering means comprises, for example, a means for defining an interior lumen running from the distal end 58 to the proximal end 60 of the sleeve 56, a hub means through which the fluid medicament is delivered to the interior lumen, and a plurality of one way valve means for communicating the fluid medicament from the interior lumen to the subcutaneous tissue 20 surrounding the sleeve 56 and for preventing fluids from entering the interior lumen.

By way of example, and referring now to FIG. 8; cylindrical sleeve 56 is illustrated as being comprised of a cylindrical outer wall 62 that is formed over a concentric cylindrical inner wall 64 in a spaced apart relationship. Thus, in this embodiment, an interior lumen 66 is provided by the space between the outer wall 62 and the inner wall 64.

By way of further example and with continued reference to FIGS. 6 and 7 in combination, the hub means is comprised of a first hub 72. In the preferred embodiment, first hub 72 is joined in a fluid tight manner to the proximal end 60 of the cylindrical sleeve 56. First hub 72 further comprises, for example, a first passageway means, such as a first hub lumen (not shown), for communicating the anesthetic agent to the interior lumen 66. As is shown in FIGS. 6 and 7, the first hub 72 can be attached, for example, to an external tube 74 through which the anesthetic agent can be introduced to the internal lumen 66, as for example by a syringe (not shown), via an infusion port 76.

FIGS. 6 through 8 further illustrate the preferred embodiment of the plurality of one way valve means spaced along the cylindrical sleeve 56. As is shown, each valve means is comprised of a one way slit 82 that is formed through outer wall 62 of cylindrical sleeve 56. These slits 82 are preferably substantially identical to the one way slits 48 described above in connection with FIGS. 1 through 3, and that discussion will not be repeated here.

As is further shown in FIGS. 6 through 8, in this particular embodiment sleeve 56 is further comprised of a means for selectively attaching and detaching the sleeve 56 from the cannula 14. For example, the means for selectively attaching and detaching is illustrated as being comprised of a continuous slit 68 that extends longitudinally along the entire length of the cylindrical sleeve 56. Slit 68 has a width such that the cylindrical sleeve 56 can be detachably mounted to the cannula 14 through the slit 68. The cylindrical sleeve 56 in such a mounted position is illustrated in FIGS. 7 and 8.

Referring now to FIG. 8, when cylindrical sleeve 56 is mounted to cannula 14, the cylindrical inner wall 64 is in continuous contact with the outer surface of cannula 14. This tight fitting position is maintained by the resilient properties that are preferably exhibited by cylindrical sleeve 56. As is further shown, the edges 69 and 69' where the outer wall 62 meets inner wall 64 are tapered with respect to the outer surface of the cannula 14. This permits the cylindrical sleeve 56 to be inserted with less trauma into the subcutaneous tissue, and it further forms a tight seal between the cylindrical sleeve 56 and cannula 14 so as to prevent bodily fluids from leaking between sleeve 56 and cannula 14. The sheath means of this embodiment is also comprised of a means for sealing the sheath means in a fluid tight manner around the cannula 14 so as to prevent fluids, such as blood from the body, from escaping between the cannula 14 and the sleeve 56. For example, as is shown in both FIGS. 6 and 7, this sealing is accomplished by placing an O-ring 70 between the cylindrical sleeve 56 and the outer surface of the cannula 14. Thus, when the cylindrical sleeve 56 is mounted to the cannula 14, O-ring 70 forms a fluid-tight seal, and thereby prevents any bodily fluids from leaking between sleeve 56 and cannula 14. Cylindrical sleeve 56 also has formed thereon a suture attachment ring 47, similar to the ring 47 discussed above in connection with FIGS. 1 through 3.

In the embodiment of FIGS. 6 and 7, the indwelling catheter apparatus further includes a second hub means, as for example hub 78, for providing fluid communication to the cannula 14. Hub 78 is joined in a fluid tight manner to the proximal end of cannula 14. As is also shown, hub 78 can be connected to external tube 80, through which fluids may be infused to cannula 14. A dilation catheter may be introduced into cannula 14 through tubing 23 and connector 25.

Figure 9:
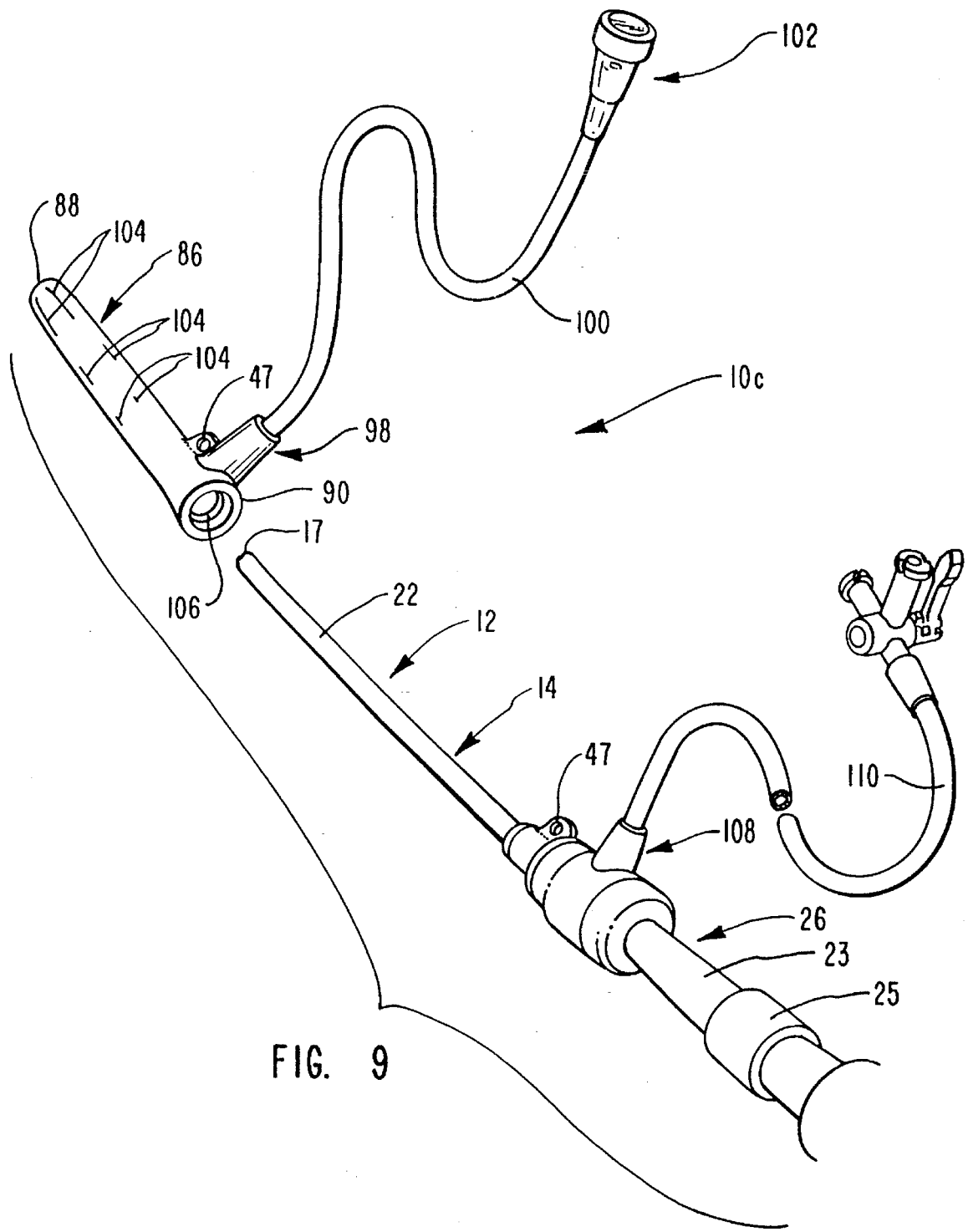
FIG. 9 is an exploded perspective view of another presently preferred embodiment of the catheter apparatus.
Figure 10:
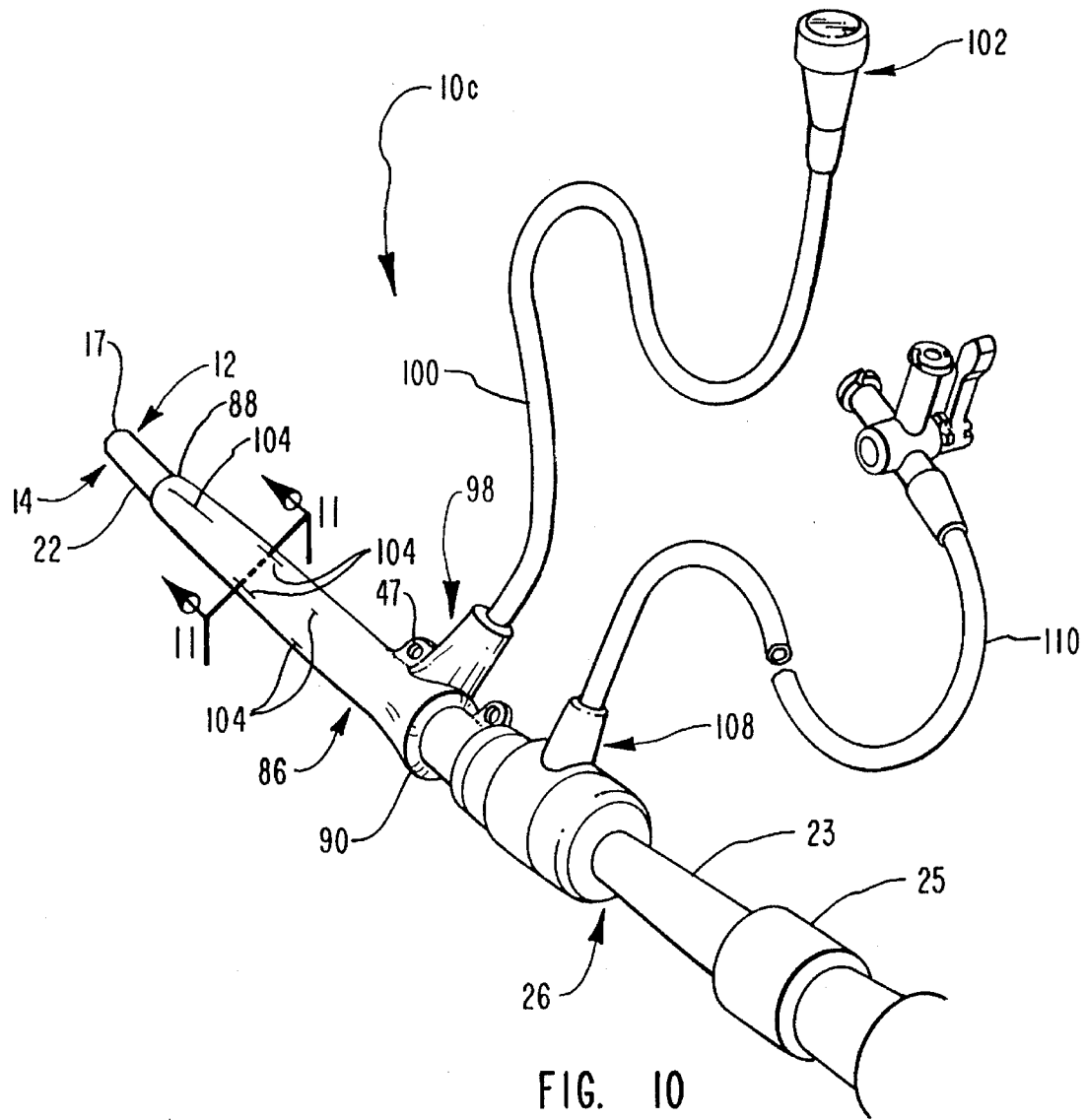
FIG. 10 is a perspective view of the anesthetizing sheath of FIG. 9 mounted to a catheter device.
Figure 11:
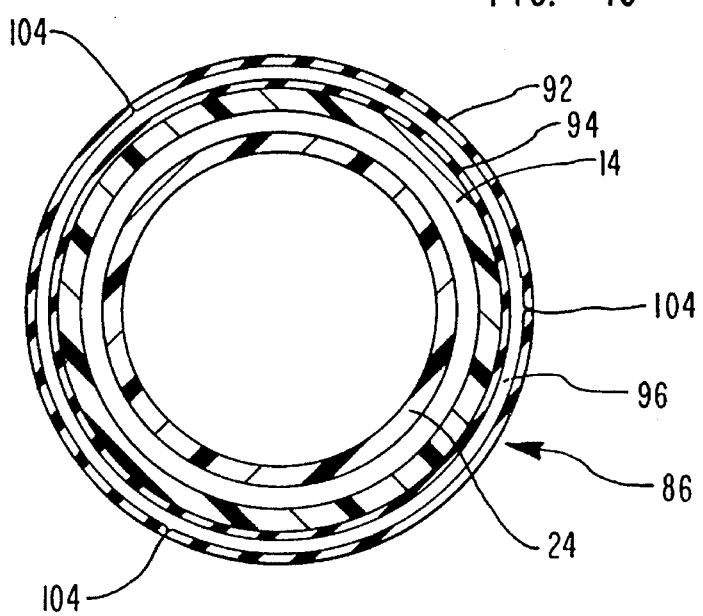
FIG. 11 is a cross-sectional view taken along line 11—11 of FIG. 10.

Yet another embodiment of the indwelling catheter apparatus of present invention is illustrated in FIGS. 9 through 11, and is designated generally at 10c. Indwelling catheter apparatus 10c also includes a catheter means, as for example a catheter device, which is essentially the same as the catheter device discussed in conjunction with FIGS. 1 through 3.

The indwelling catheter apparatus 10c also comprises a sheath means, as for example a hollow cylindrical sleeve 86, for placement onto at least a portion of the cannula 14 at a point intermediate of the distal end 17 and the proximal hub end 26 of the cannula 14. As with the embodiment shown in FIGS. 6 through 8, the sheath means of FIGS. 9 through 11 can be selectively attached and detached to the cannula 14, as will be discussed in further detail below.

As is shown in FIGS. 9 and 10, cylindrical sleeve 86 has a distal 88 and a proximal end 90. Hollow cylindrical sleeve 86 further has an inner diameter which is greater than the outer diameter of cannula 14. This relationship is also shown in the cross-sectional view of FIG. 11. Also shown in FIG. 11 is cylindrical sleeve 86 positioned in a tight fitting manner on cannula 14 so as to be concentric with the cannula 14. Preferably, distal end 88 of cylindrical sleeve 86 is tapered with respect to the outer surface of cannula 14, so that the cylindrical sleeve 86 can be inserted with little or no trauma through the portion of subcutaneous tissue 20 when it is mounted to the cannula 14.

The cylindrical sleeve 86 further comprises a means for delivering fluid medicament, such as an anesthetic agent (not shown), to the subcutaneous tissue 20 surrounding the sleeve 86. The fluid medicament delivering means comprises, for example, a means for defining an interior lumen running from the distal end 88 to the proximal end 90 of the sleeve 86, a hub means through which the fluid medicament is delivered to the interior lumen, and a plurality of one way valve means for communicating the fluid medicament from the interior lumen to the subcutaneous tissue surrounding the sheath means and for preventing fluids from entering the interior lumen.

By way of example, and referring now to FIG. 11, cylindrical sleeve 86 is illustrated as being comprised of a cylindrical outer wall 92 that is formed over a concentric cylindrical inner wall 94 in a spaced apart relationship. Thus, in this embodiment, interior lumen 96 is provided by the space which is formed between the outer wall 92 and the inner wall 94.

By way of further example and with reference now to FIGS. 9 and 10 in combination, the hub means is comprised of a first hub 98 joined in a fluid tight manner to the proximal end 90 of the cylindrical sleeve 86. First hub 98 further comprises, for example, a first passageway means, such as a first hub lumen (not shown), for communicating the fluid medicament to the interior lumen 96. As is shown in FIGS. 9 and 10, the first hub 98 can be attached, for example, to an external tube 100 through which the fluid medicament can be introduced to the internal lumen 96, as for example by syringe (not shown), via an infusion port 102.

FIGS. 9 through 11 further illustrate the preferred embodiment of the plurality of one way valve means spaced along the cylindrical sleeve 86. As is shown, each valve means is comprised of a one way slit 104 that is formed through outer wall 92 of cylindrical sleeve 86. These slits 104 are preferably substantially identical to the one way slits 48 described above in connection with FIGS. 1 through 3.

As is further shown in FIGS. 9 and 10, in this particular embodiment the sleeve 86 is further comprised of a means for selectively attaching and detaching the cylindrical sleeve 86 from the cannula 14. For example, selective attachment and detachment is illustrated as being accomplished by longitudinally sliding the hollow cylindrical sleeve 86 onto cannula 14. The cylindrical sleeve 86 in such a mounted position is illustrated in FIGS. 10 and 11.

When cylindrical sleeve 86 is thus mounted to cannula 14, the cylindrical inner wall 94 is in a continuous and tight fitting contact with the outer surface of cannula 14. The inner diameter of the cylindrical sleeve 86 with respect to the outer diameter of cannula 14 is such that the sleeve 86 remains positioned on the cannula 14 in a slidable, yet tight fitting manner.

The sleeve 86 of this embodiment is also comprised of a means for sealing the sleeve 86 in a fluid tight manner around the cannula 14 so as to prevent fluids, such as blood from the body, from escaping between the cannula 14 and the sleeve 86. For example, as is shown in FIG. 9, this sealing means is accomplished by placing an O-ring 106 between the inner surface of the cylindrical sleeve 86 and the outer surface of the cannula 14. Thus, when the cylindrical sleeve 86 is mounted to the cannula 14, O-ring 106 forms a fluid-tight seal, and thereby prevents any bodily fluids from leaking between sleeve 86 and cannula 14. Cylindrical sleeve 86 also has formed thereon a suture attachment ring 47, similar to the ring 47 discussed above in connection with FIGS. 1 through 3.

In the embodiment of FIGS. 9 and 10, the indwelling catheter apparatus further includes a second hub means, as for example hub 108, for providing fluid communication to the cannula 14. Hub 108 is joined in a fluid tight manner to proximal hub end 26 of cannula 14. As is also shown, hub 108 can be connected to external tube 110, through which fluids may be infused to cannula 14.

As discussed, the cylindrical sleeves 56, 86 of the two embodiments of FIGS. 6 through 8 and 9 through 11 are not permanently mounted to any particular catheter device 12, but can be selectively attached and detached to preexisting catheter devices. Consequently, the versatility of a single cylindrical sleeve is greatly enhanced because it can be used with any one of a variety of catheter devices that are already on hand. Thus, when using a preexisting catheter device, medical personnel can retrofit the device with a cylindrical sleeve discussed in connection with FIGS. 6 through 11, and provide the patient with the pain relief that would not otherwise be available with that catheter device. Importantly, this retrofit capability provides the advantages of pain relief, yet simultaneously protects any investment already made in a stock of preexisting catheter devices.

It will be appreciated that although the only difference between the embodiment of FIGS. 6 through 8 and the embodiment of FIGS. 9 through 11 lies in how the cylindrical sleeve 56 or 86 is attached and detached to the cannula 14, the difference in how the two embodiments are used is more significant. In use, cylindrical sleeve 56 (FIGS. 6–8) attaches and detaches to the cannula 14 by way of the longitudinal slit 68 formed along the length of the sleeve 56. Thus, the sleeve 56 can be attached to a cannula 14 even if the cannula 14 has already been inserted in the patient. For instance, a doctor may insert a catheter device, such as an insertion sheath, perform the underlying procedure and, when completed, snap on the cylindrical sleeve 56 to the proximal portion of the cannula 14. Since the patient is still locally anesthetized from the previously performed medical procedure, the sleeve 56 can then be inserted into the portion of subcutaneous tissue 20 with the cannula 14. When the cannula 14 is later retracted (and the previously administered local anesthetic has worn off) the doctor can readminister a local anesthetic to the subcutaneous tissue 20 through sleeve 56 and then painlessly retract the cannula 14. In this way, the doctor or medical technician is not distracted by the extra equipment, tubes, infusion ports, etc. associated with cylindrical sleeve 56 while the underlying medical procedure, such as a PTCA, is being done.

In contrast, cylindrical sleeve 86 (FIGS. 9–11) attaches and detaches to the cannula 14 by sliding the sleeve 86 onto the cannula 14. Consequently, the sleeve 86 of this embodiment cannot be placed on a cannula 14 that has already been inserted in a patient, and must necessarily be positioned on the cannula 14 before the underlying medical procedure is done and thus before cannula 14 is initially inserted into the patient. However, under certain circumstances this approach may be entirely acceptable and/or desirable.

Figure 12:
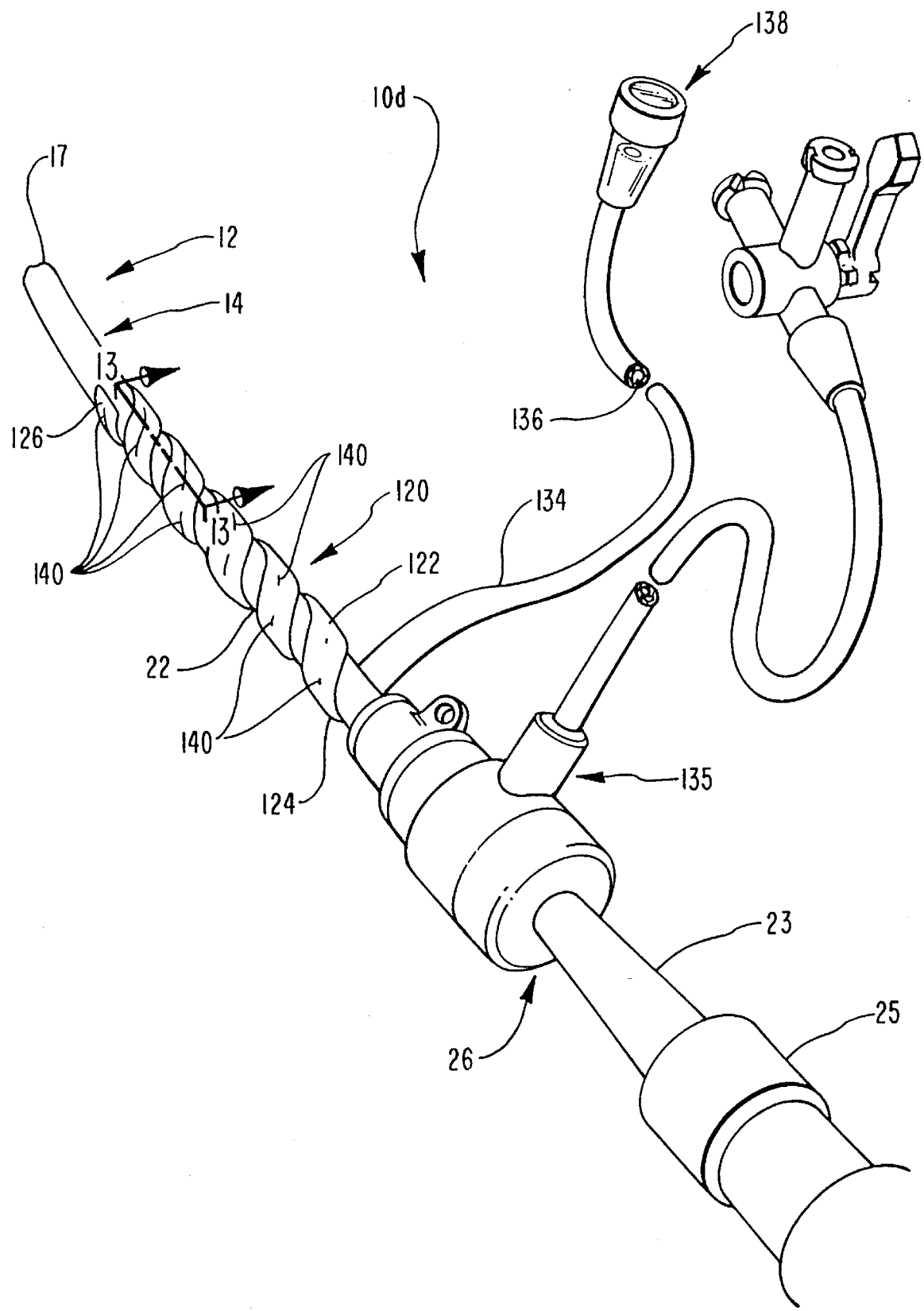
FIG. 12 is a perspective view of still another embodiment of the present invention.
Figure 13:
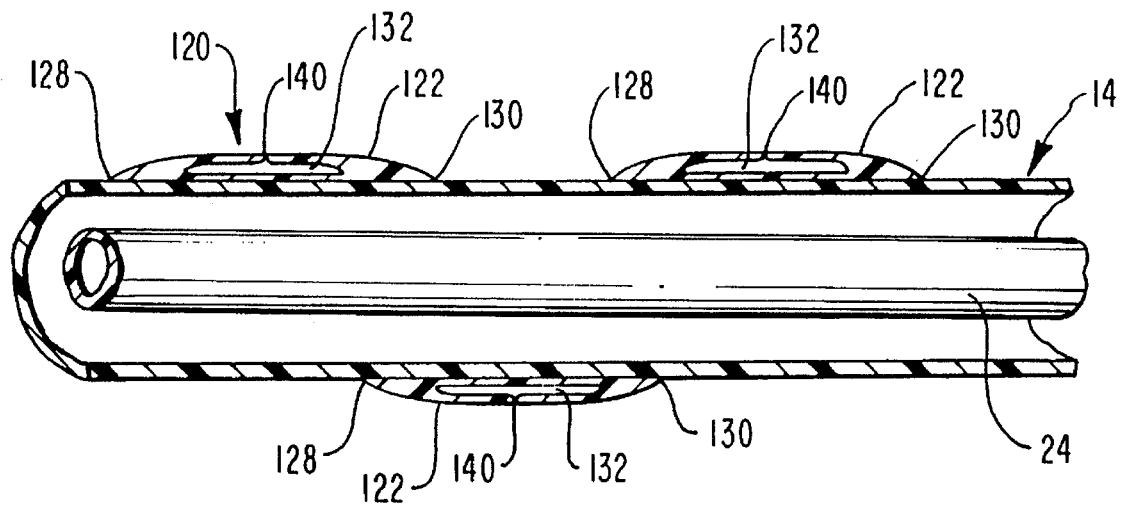
FIG. 13 is an enlarged cross-sectional view taken along lines 13—13 of FIG. 12.

FIGS. 12 and 13 illustrate yet another embodiment of the indwelling catheter apparatus of the present invention, designated generally at 10d. As in the embodiments previously discussed, catheter apparatus 10d includes a catheter means, as for example a catheter device, which is essentially the same as the catheter device of the previous embodiments.

The indwelling catheter apparatus 10d also has a sheath means for placement onto the cannula 14. By way of example and referring now to FIG. 12, sheath means is comprised of a helical sheath, designated generally at 120. As is shown, helical sheath 120 is comprised of a single band 122 that is wound in a helical fashion so as to conform to the cylindrical outer periphery of the cannula 14. The helical sheath 120 has a proximate end 124 and a distal end 126, and is preferably positioned on the cannula 14 so that it can be disposed within the area of subcutaneous tissue 20 in conjunction with the cannula 14 (in the same manner illustrated in FIG. 2).

Referring now to FIG. 13, the band 122 that forms helical sheath 120 has a substantially flat cross-section when it is placed on the cannula 14. Further, when positioned on the cannula 14, band 122 has successive leading edges 128 and trailing edges 130 that are tapered with respect to the outer surface of the cannula 14. Advantageously, when the helical sheath 120 is mounted to the cannula 14, this flat cross-section and the tapered leading and trailing edges 128, 130 of band 122 act so as to ease the insertion and retraction of the helical sheath 120 through the patient's skin and subcutaneous tissue 20 when it is mounted to the cannula 14. Similarly, this configuration minimizes trauma to the skin or subcutaneous tissue 20 when the helical sheath 120 is inserted and retracted.

Figure 13A:
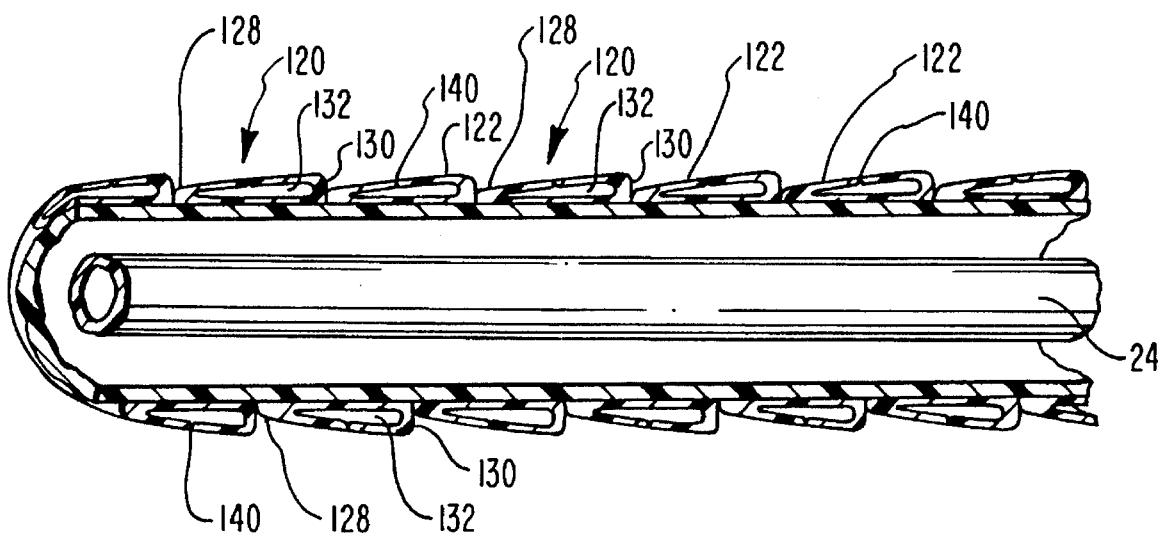
FIG. 13A is an enlarged cross-sectional view showing an alternative embodiment of the catheter apparatus of FIG. 12.

Alternatively, FIG. 13A illustrates another cross-sectional shape that may be formed by band 122. In this embodiment, band 122 is placed on cannula 14 in a tight helical fashion such that the leading edges 128 abut against the adjacent trailing edges 130. Further, each leading edge 128 slopes upwardly towards the trailing edge 130 to form an overall tapered shape. In this way, the helical sheath 120 has an overall tapered shape so as to permit easier insertion through the patient's skin and subcutaneous tissue 20.

Helical sheath 120 is further comprised of a fluid medicament delivery means for delivering a fluid medicament, such as an anesthetic agent, to the subcutaneous tissue 20 in which the helical sheath 120 is disposed. By way of example, FIGS. 12 and 13 illustrate how the fluid medicament delivery means is preferably comprised of a means for defining an interior lumen running from the distal end 126 to the proximate end 124 of helical sheath 120. As is shown, lumen means is comprised of an interior lumen 132 that is defined by a hollow portion formed within band 122. The hollow portion that defines interior lumen 132 extends along the entire length of helical sheath 120.

Helical sheath 120 is also preferably comprised of a hub means through which the anesthetic agent is delivered to the interior lumen 132. As FIG. 12 illustrates, hub means is comprised, for example, of a tube 134 which is coupled in a fluid tight manner to the proximal end 124 of the helical sheath 120. Tube 134 has a single lumen 136 that is in fluid communication with the interior lumen 132. Anesthetic agent can be delivered to interior lumen 132 through a fluid injection port 138 connected to the opposite end of tube 134. FIG. 12 further illustrates how hub means also comprises, for example, a hub 135 that is connected in a fluid tight manner to the proximal hub end 26 of cannula 14. Hub 135 is essentially identical to hub 108 discussed in connection with the embodiment of FIG. 10, and thus that discussion will not be repeated.

With continued reference to FIG. 12, helical sheath 120 also comprises a plurality of one way valve means for communicating the anesthetic agent from the interior lumen 132 to the subcutaneous tissue 20 surrounding the sheath 120, and at the same time, for preventing bodily fluids, such as blood, from entering the interior lumen 132. For example, FIGS. 12 and 13 illustrate how the valve means are each comprised of a one way slit 140 that is formed through the band 122 to interior lumen 132. One way slits 140 are placed uniformly along helical sheath 120, and are essentially identical to the one way slits discussed above in connection with the embodiments of FIGS. 1 through 11.

As discussed generally, helical sheath 120 may further comprise a means for selectively attaching and detaching the helical sheath 120 to the cannula 22. This function is provided by wrapping the helical sheath 120 onto the longitudinal length of cannula 14 so that the helical sheath 120 is concentrically positioned on the cannula, as is illustrated in FIG. 12. It will be appreciated that, like the embodiment of FIGS. 6 through 8, helical sheath 120 can be detachably mounted to a cannula 14 even after the cannula 14 has already been inserted into the patient. Preferably, the helical sheath 120 exhibits sufficient resilient properties such that once it is positioned on the cannula 14, it remains positioned in a tight fitting manner. Alternatively, once helical sheath 120 has been detachably mounted to the cannula 14, the medical technician may further adhere the sheath 120 to the cannula 14 by applying a small amount of liquid adhesive. Thus, helical sheath 120 can be selectively used on a variety of preexisting catheter devices. Alternatively, cannula 14 can be manufactured with a helical sheath 120 premounted in the manner illustrated in FIG. 12. In this instance, helical sheath 120 would be affixed permanently to the catheter device 12 by fusing, or similarly adhering it to the cannula 14.

Figure 14:
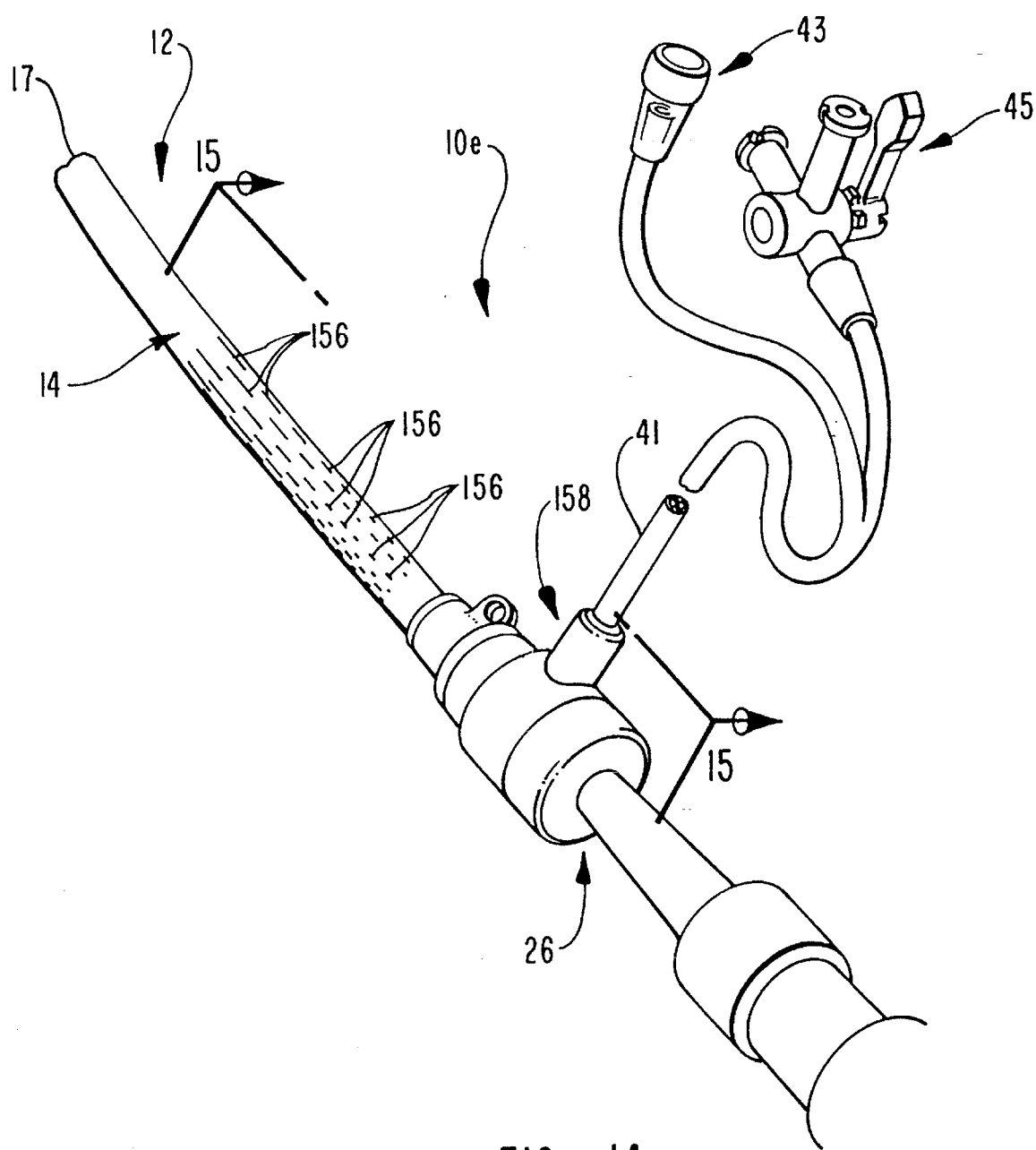
FIG. 14 is a perspective view of yet another embodiment of a catheter apparatus constructed in accordance with the inventive concepts of the present invention.
Figure 15:
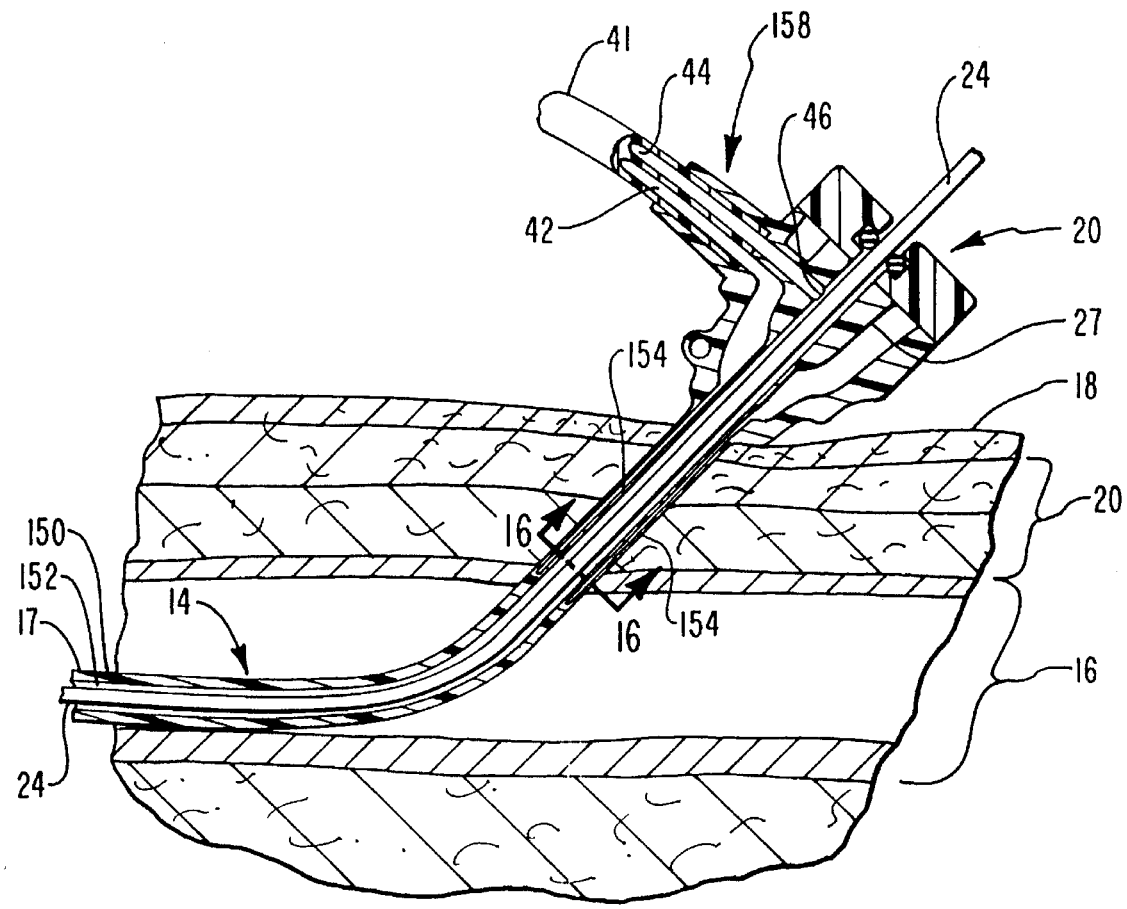
FIG. 15 is a cross-sectional view taken along lines 15—15 of FIG. 14, and further illustrates the catheter apparatus of FIG. 14 disposed within a portion of a patient's body.
Figure 16:
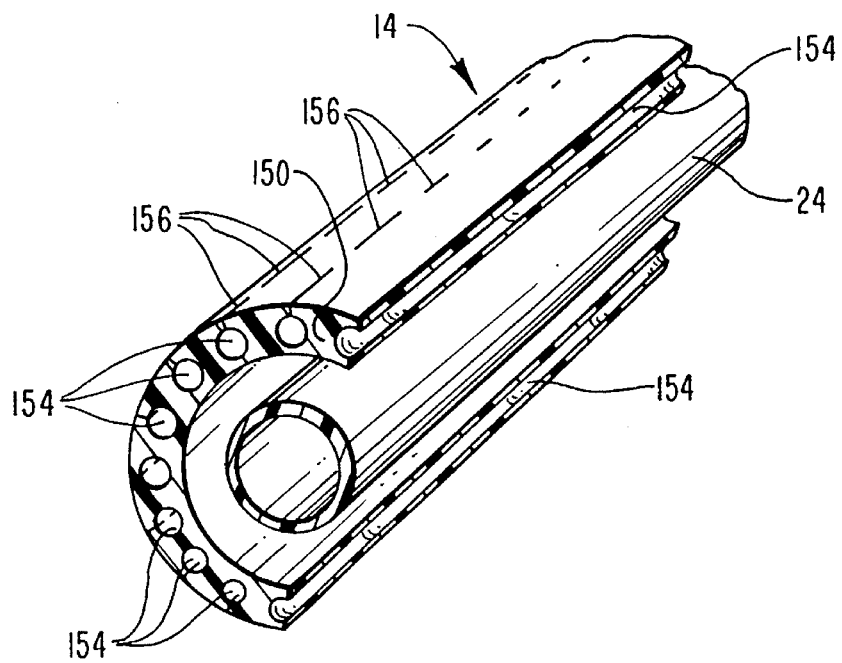
FIG. 16 is an enlarged cross-sectional view taken along lines 16—16 of FIG. 15.

Referring now to FIGS. 14 through 16, yet another preferred embodiment of indwelling catheter apparatus, designated generally at 10e, is shown. Indwelling catheter apparatus 10e includes a catheter means, as for example a catheter device 12, that has a cannula 14 for insertion through subcutaneous tissue 20 into a patient's body (shown in FIG. 15). The catheter device 12 is essentially identical to the catheter device described in conjunction with the previous embodiments, having an indwelling distal end 17 and a proximal hub end 26. FIG. 15 further illustrates how cannula 14 is a cylindrical tube having a cylindrical outer wall 150, through which a primary lumen 152 runs.

Indwelling catheter apparatus 10e also comprises a means for delivering a fluid medicament, such as an anesthetic agent, to essentially only the area of subcutaneous tissue 20 through which the cannula 14 is inserted. For example, in the embodiment of FIGS. 14 through 16, the means for delivering a anesthetic agent is comprised of a secondary lumen that is formed in the outer wall 150 of the cannula 14. FIGS. 15 and 16 illustrate how the secondary lumen is preferably comprised of a plurality of longitudinal bores 154 formed within the outer wall 150. As is further shown, the plurality of bores 154 are uniformly spaced about the circumference of the cannula 14, and each bore 154 is substantially parallel to the primary lumen 152 running through the cannula 14. Further, the plurality of bores 154 that form the secondary lumen are preferably formed in the cannula 14 outer wall 150 so that they are substantially disposed within the area of subcutaneous tissue 20 once the cannula 14 has been inserted within the patient's body. In this way, secondary lumen, as defined by the plurality of bores 154, can distribute the anesthetic agent to the subcutaneous tissue 20 evenly and uniformly.

The anesthetic agent is communicated to the surrounding subcutaneous tissue 20 from the secondary lumen 154 through a plurality of one way valve means, which also act to prevent bodily fluids from entering the secondary lumen 154. As FIG. 14 illustrates, the one way valve means are each comprised of a single one way slit 156 that is formed through the outer wall 150 to each of the plurality of longitudinal bores 154. This is illustrated in further detail in the exploded cross-section view of FIG. 16, where one way slits 156 are illustrated. Each of the one way slits 156 are substantially identical to the one way slits discussed above in connection with the other preferred embodiments.

To deliver the anesthetic agent to the secondary lumen 154, the fluid medicament delivery means is further comprised of a hub means. This hub means is illustrated as being comprised of a single hub 158, that is joined in a fluid tight manner to the proximal hub end portion 27 of the cannula 14. FIGS. 14 and 15 illustrate how hub 158 is formed with a first hub lumen 42 and a second hub lumen 44. First hub lumen 42 is coupled to each of the longitudinal bores 154 that form the secondary lumen so as to provide a passageway for delivering anesthetic agent. Similarly, second hub lumen 44 is coupled to the primary lumen 152 via a cannula access hole 46, thereby providing a separate fluid passageway for that lumen. As FIG. 14 illustrates, the first and second hub lumens 42, 44 are connected to a multi-lumen tube 41, through which the first hub lumen 42 is connected to an infusion port 43, and second hub lumen 44 is connected to an I.V. valve assembly 45. Thus, anesthetic agent can be delivered to the bores 154 that form the secondary lumen with a syringe by using infusion port 43.

Figure 17A:
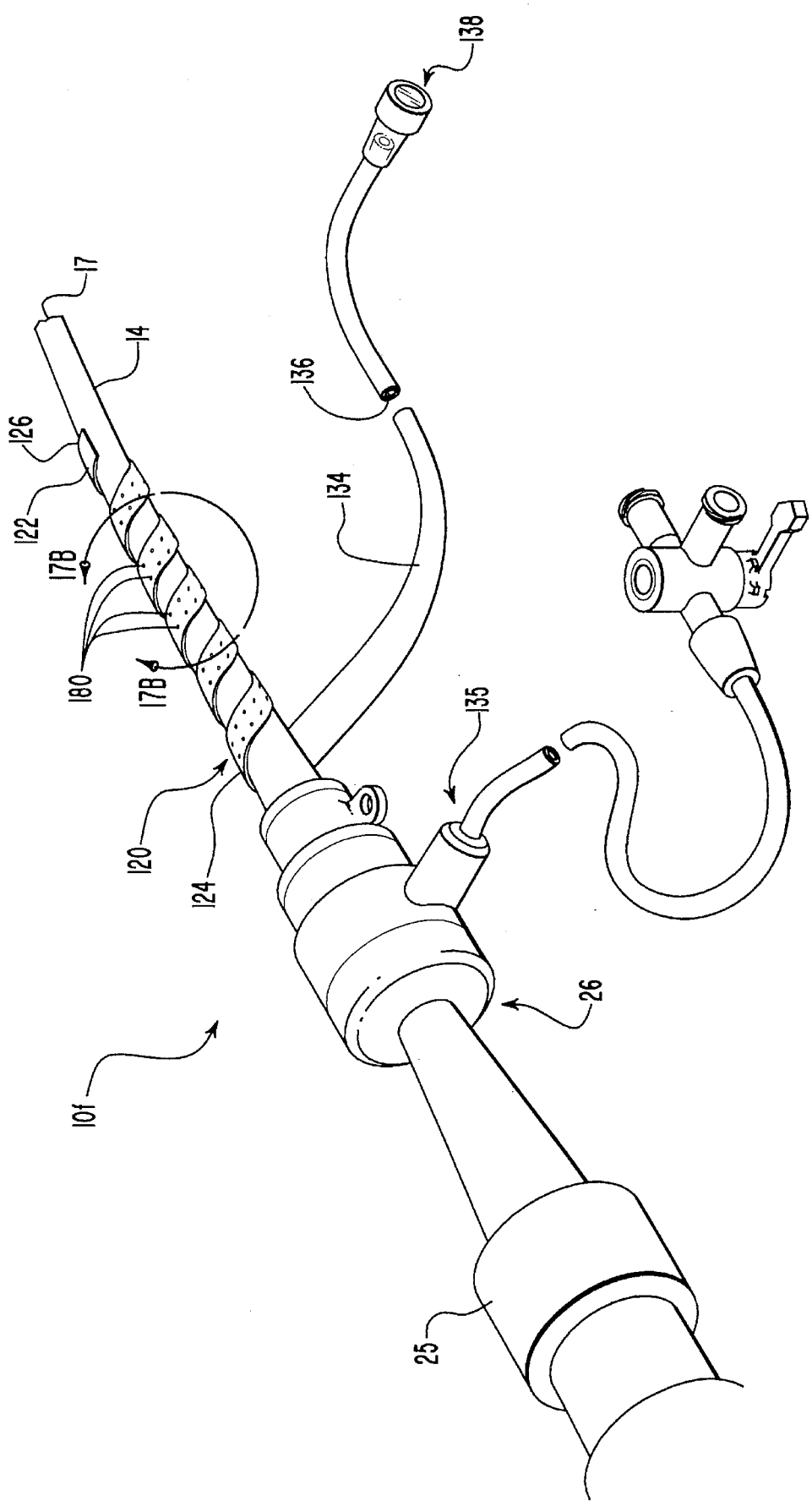
FIG. 17A is a perspective view of yet another presently preferred embodiment of the anesthetizing sheath mounted to a catheter device.

Referring next to FIGS. 17A–B and 18A–B, yet another embodiment of the present invention is shown. FIG. 17A illustrates an indwelling catheter apparatus 10f having a sheath means that is comprised of a hollow elongate band, wrapped in a helical fashion about cannula 14. This helical sheath, designated at 120, is substantially identical to the helical sheath 120 shown in FIG. 12. The identical portions of that device are designated with like numerals in FIG. 17A, and their description will not be repeated. However the embodiment of FIG. 17A differs from that of FIG. 12 in the manner by which the valve means is constructed.

Figure 17B:
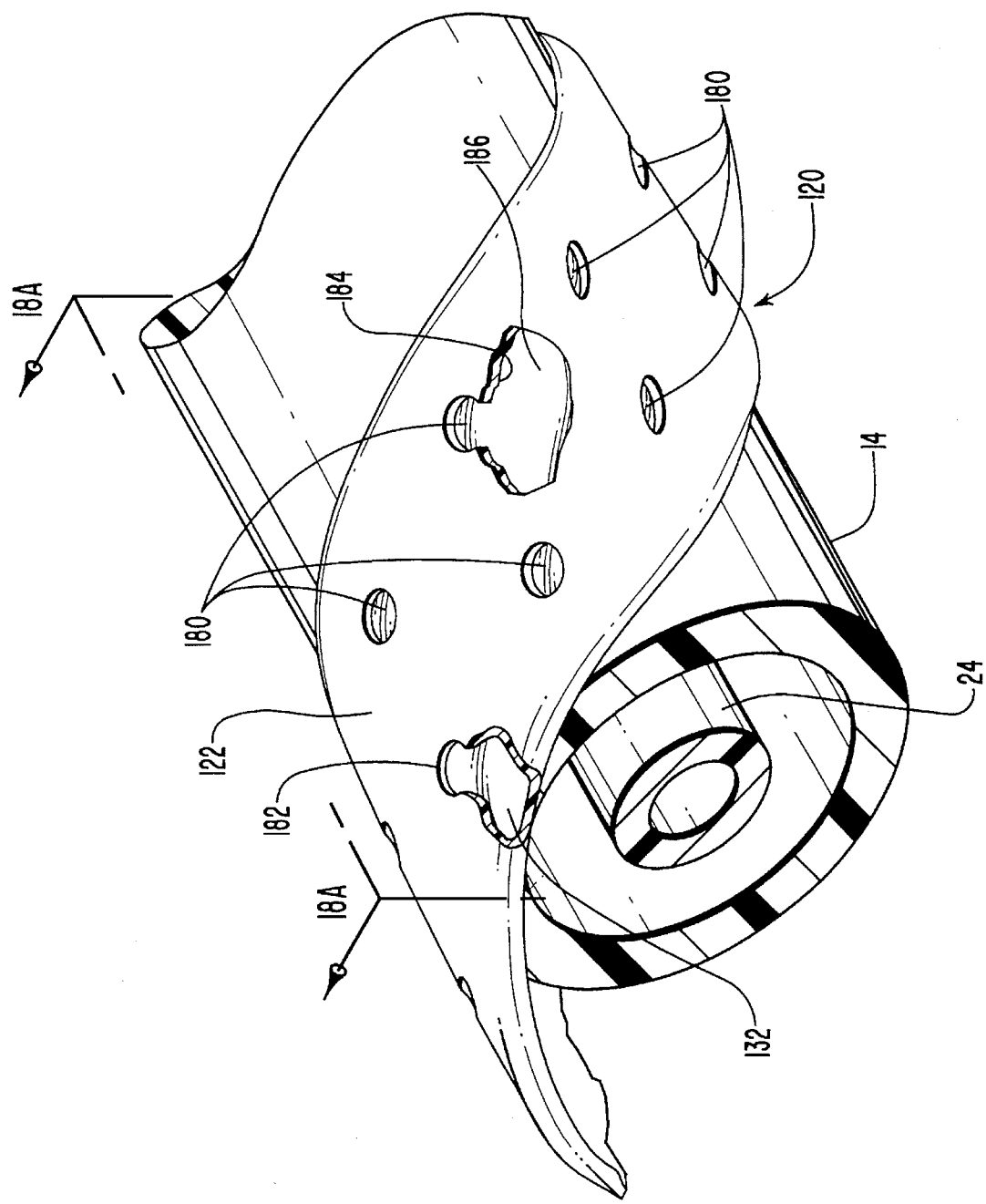
FIG. 17B is an enlarged perspective view in partial cross-section taken along lines 17B—17B of FIG. 17A.
Figure 18A:
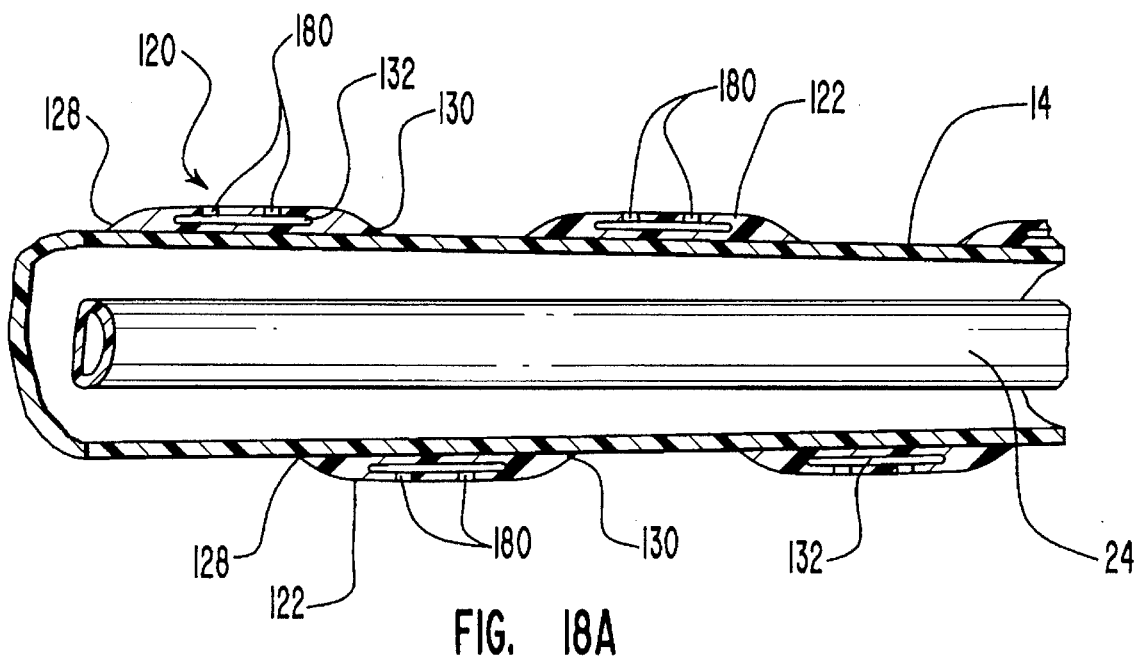
FIG. 18A is an enlarged cross-sectional view taken along lines 18A—18A of FIG. 17B.
Figure 18B:
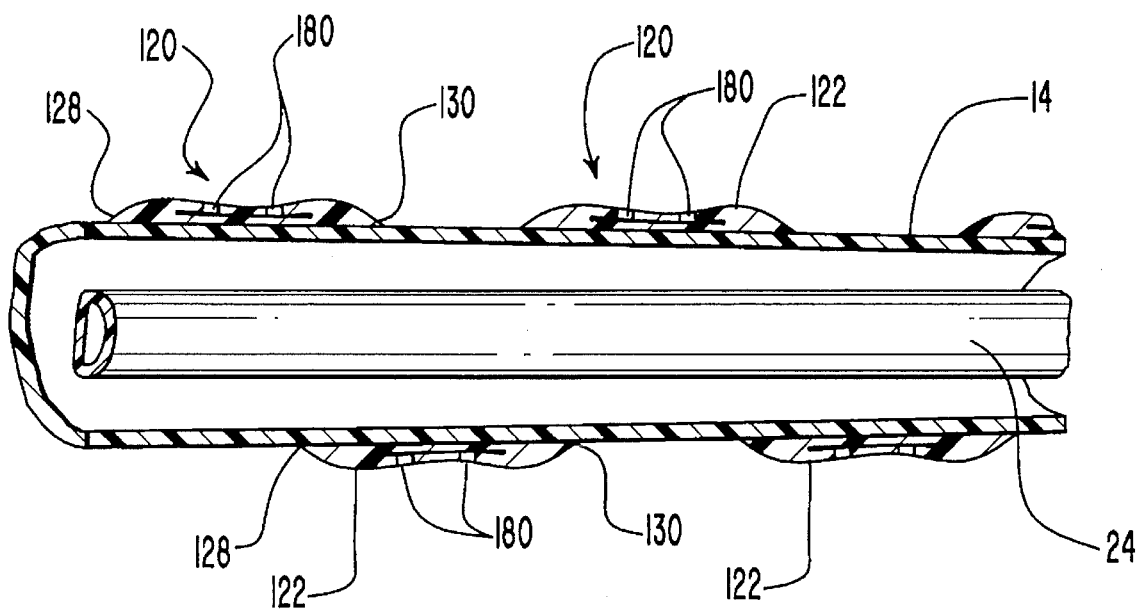
FIG. 18B is an enlarged cross-sectional view also taken along lines 18A—18A of FIG. 17B, illustrating the manner by which the interior lumen is compressed so as to close the delivery holes and thereby prevent the entry of bodily fluids into the lumen.

As is shown by way of example in FIG. 17A, in this particular embodiment the valve means is comprised of a plurality of delivery holes, designated at 180, which are substantially circular in shape and arranged uniformly along the length of the elongate band 122 that forms the helical sheath 120. FIG. 17B illustrates in further detail how each circular hole 180 is formed completely through the outer surface 182 of the band 122 so as to provide a fluid communication path with the interior lumen 132 formed within the band 122. Each hole 180 acts as a fluid path for delivering the anesthetic agent, or similar fluid medicament, to the subcutaneous tissue that is coextensive with the helical sheath 120 when it is inserted into the patient.

In the preferred embodiment, the helical sheath 120 is constructed of a slightly flexible material, such as a polyurethane, Teflon, polyethylene, or similarly flexible and medically suitable material. When fluid medicament is to be delivered to the subcutaneous tissue 20 of a patient, a positive fluid pressure is generated within the interior lumen 132, as for example by way of a syringe (not shown) that is connected to the injection port 138. In this pressurized state, illustrated in cross-section in FIG. 18A, the interior lumen 132 expands and thereby opens each of the holes 180. In this "open state," fluid medicament is delivered from the interior lumen 132, through the open delivery holes 180, and to the subcutaneous tissue 20.

The delivery holes 180 also prevent bodily fluids and/or fluid medicament from re-entering the interior lumen 132.

The flexibility of the material used to form the helical sheath 120 and the size of the holes 180 together act to perform this function. When the sheath 120 is positioned within the subcutaneous tissue 20 and medicament is not being delivered, there is no fluid pressure present within the lumen 132. Instead, the pressure exerted on the exterior surface 182 of the sheath 120, such as that which would be caused by the surrounding subcutaneous tissue 20 and the interstitial blood pressure, compresses the interior lumen 132 and causes the lumen walls 184, 186 (shown in FIG. 17B) to collapse against one another. This condition is best seen in the cross-sectional illustration of FIG. 18B. As is shown in this compressed state, the delivery holes 180 no longer provide a fluid communication path to the interior lumen 132, and external bodily fluids are thereby prevented from entering the lumen 132.

In the preferred embodiment, each of the delivery holes 180 are generally circular in shape, and are all of the same approximate diameter. However, it will be appreciated that the holes 180 can have various different shapes and yet provide the function described above. Also, if desired the hole 180 sizes can be varied, thereby controlling the amount of medicament that is delivered to the subcutaneous tissue 20.

Also, although this embodiment discloses the use of delivery holes 180 on a helical sheath 120, it will be appreciated that the holes 180 could also be used in conjunction with the other sheath embodiments described above.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. An indwelling catheter apparatus comprising:
    catheter means for insertion through subcutaneous tissue, said catheter means comprising an indwelling cannula adapted for insertion through subcutaneous tissue into a patient's body, and having an indwelling distal end and a proximal hub end adapted for securement outside of the body; and
    sheath means for placement over and around at least a portion of said cannula and into but essentially not beyond the subcutaneous tissue after the cannula is inserted, and for delivering fluid medicament to essentially only the subcutaneous tissue surrounding said cannula, said sheath means including a plurality of delivery holes, each of said delivery holes providing a fluid communication path between the sheath means and the surrounding subcutaneous tissue for said fluid medicament.

2. An indwelling catheter apparatus as defined in claim 1 wherein said cannula is comprised of a cylindrical tube having a cylindrical outer wall, and wherein a primary lumen runs through said tube, and wherein said sheath means comprises at least one interior lumen, and wherein the plurality of delivery holes are formed on the sheath means so as to each be in fluid communication with said at least one interior lumen.

3. An indwelling catheter apparatus as defined in claim 2 wherein said sheath means further comprises hub means for delivering the fluid medicament to said at least one interior lumen.

4. An indwelling catheter apparatus as defined in claim 3 wherein said hub means comprises an infusion port, the infusion port being in fluid communication with the at least one interior lumen.

5. An indwelling catheter apparatus as defined in claim 3 wherein said hub means comprises first passageway means for communicating the fluid medicament to said interior lumen, and second passageway means for providing fluid communication to said primary lumen.

6. An indwelling catheter apparatus as defined in claim 1 wherein the sheath means comprises means for sealing the sheath means in a fluid tight manner around the cannula so as to prevent fluids from the body from escaping between the cannula and the sheath means.

7. An indwelling catheter apparatus as defined in claim 1 wherein the sheath means is comprised of a cylindrical member having at least one interior lumen formed therein, and wherein the plurality of delivery holes are formed on the cylindrical member so as to be in fluid communication with the at least one interior lumen.

8. An indwelling catheter apparatus as defined in claim 1 wherein the sheath means is comprised of a cylindrical member having at least one interior lumen formed therein, and wherein the plurality of delivery holes are formed on the cylindrical member so as to be in fluid communication with the at least one interior lumen, the cylindrical member further having a means for selectively attaching and detaching the cylindrical member from said cannula.

9. An indwelling catheter apparatus as defined in claim 1 wherein the sheath means is comprised of an elongate band wrapped in a helical fashion around said cannula.

10. An indwelling catheter apparatus as defined in claim 9 wherein at least one interior lumen is formed within said elongate band and wherein the plurality of delivery holes are formed on the elongate band so as to be in fluid communication with said interior lumen.

11. An indwelling catheter apparatus comprising:
    catheter means for insertion through subcutaneous tissue, said catheter means comprising an indwelling cannula adapted for insertion through subcutaneous tissue into a patient's body, and having an indwelling distal end and a proximal hub end adapted for securement outside of the body; and
    sheath means for placement over and around the outer circumference of at least a portion of said cannula intermediate said distal and proximal ends after the cannula is inserted, such that said sheath means is capable of being inserted into but essentially not beyond the subcutaneous tissue, said sheath means having distal and proximal ends and comprising means for defining an interior lumen running from the distal to the proximal end of the sheath means, and said sheath means further comprising:
    a plurality of delivery holes, spaced along said sheath means from the distal to the proximal end thereof, each of the delivery holes providing a fluid communication path between said interior lumen and the surrounding subcutaneous tissue; and
    hub means for delivering fluid medicament to said interior lumen.

12. An indwelling catheter apparatus as defined in claim 11 wherein said sheath means comprises a cylindrical sleeve having the interior lumen formed therein, and wherein the cylindrical sleeve is placed on the cannula so as to be concentric with said cannula.

13. An indwelling catheter apparatus as defined in claim 11 wherein said sheath means comprises an elongate band, the elongate band being wrapped over and around the outer circumference of the cannula in a helical manner, and wherein the interior lumen is formed within the elongate band.

14. An indwelling catheter apparatus as defined in claim 12 wherein the cylindrical sleeve is affixed to said cannula.

15. An indwelling catheter apparatus as defined in claim 13 wherein the elongate band is affixed to said cannula.

16. An indwelling catheter apparatus as defined in claim 13 wherein the elongate band is joined in a fluid tight manner to said hub means at the proximal end of said elongate band, and wherein said hub means comprises first passageway means for communicating the fluid medicament to said interior lumen.

17. An indwelling catheter apparatus as defined in claim 16 wherein the hub means comprises an infusion port, the infusion port being in fluid communication with the interior lumen.

18. An indwelling catheter apparatus as defined in claim 11 wherein said sheath means further comprises means for selectively attaching and detaching the sheath means over and around the outer circumference of the cannula.

19. A catheter apparatus for insertion through subcutaneous tissue into a patient's body so as to be indwelling within the body, and for delivery of anesthetic agents to subcutaneous tissue surrounding the indwelling catheter apparatus prior to removal thereof to minimize pain to the patient upon removal of the indwelling catheter apparatus, comprising:

catheter means for insertion through subcutaneous tissue, said catheter means comprising an indwelling cannula adapted for insertion through subcutaneous tissue into a patient's body, and having an indwelling distal end and a proximal hub end adapted for securement outside of the body;

an elongate band having distal and proximal ends, the band being wrapped over and around the outer circumference of the cannula in a helical manner so as to be capable of being inserted into but essentially not beyond the subcutaneous tissue, the elongate band further comprising:

an interior lumen formed within the band and extending from the distal to the proximal end of the band;

a plurality of delivery holes spaced uniformly along the length of the elongate band, each of said delivery holes being substantially circular in shape, and formed through the outer surface of the band so as to provide a fluid communication path between the interior lumen and the surrounding subcutaneous tissue; and hub means for delivering the fluid medicament to the interior lumen.

20. An improved catheter apparatus having a cannula adapted for insertion through subcutaneous tissue into a patient's body so as to be indwelling within the body, and wherein the improvement comprises:

sheath means for placement onto at least a portion of the indwelling cannula and for delivery of anesthetic agents to subcutaneous tissue surrounding the indwelling cannula and sheath means prior to removal of the cannula so as to minimize pain to the patient upon removal of the indwelling cannula, said sheath means having distal and proximal ends and comprising means defining an interior lumen running from the distal to the proximal end of the sheath means, and said sheath means further comprising means for selective attachment and detachment from said cannula, and a plurality of delivery holes, spaced uniformly along said sheath means from the distal to the proximal end thereof, each of which form a fluid communication path between said lumen and the subcutaneous tissue surrounding said sheath means for delivery of the anesthetizing agents; and hub means, joined to the proximal end of the sheath means, for delivering the anesthetizing agents to the interior lumen of said sheath means.

* * * * *